(12) United States Patent
Tasch

(10) Patent No.: US 9,636,046 B2
(45) Date of Patent: May 2, 2017

(54) DIAGNOSIS SYSTEM AND METHOD

(75) Inventor: Uri Tasch, Baltimore, MD (US)

(73) Assignee: Step Analysis LLC, Baltimore, MD (US)

( * ) Notice: Subject to any disclaimer, the term of this patent is extended or adjusted under 35 U.S.C. 154(b) by 1467 days.

(21) Appl. No.: 12/497,907

(22) Filed: Jul. 6, 2009

(65) Prior Publication Data

US 2010/0217157 A1 Aug. 26, 2010

Related U.S. Application Data

(60) Provisional application No. 61/154,893, filed on Feb. 24, 2009.

(51) Int. Cl.
*A61B 5/103* (2006.01)

(52) U.S. Cl.
CPC .................. *A61B 5/1038* (2013.01)

(58) Field of Classification Search
CPC ..... A61B 5/1036–5/1038; A61B 5/112; G01G 21/23; G01L 1/26
USPC .................................................. 600/587, 595
See application file for complete search history.

(56) References Cited

U.S. PATENT DOCUMENTS

| | | | |
|---|---|---|---|
| 3,894,437 A * | 7/1975 | Hagy et al. | 73/865.4 |
| 4,601,356 A * | 7/1986 | Muccillo, Jr. | 177/211 |
| 5,299,454 A * | 4/1994 | Fuglewicz et al. | 73/172 |
| 6,699,207 B2 | 3/2004 | Tasch et al. | |
| 6,899,686 B2 * | 5/2005 | Hampton et al. | 600/595 |
| 6,916,295 B2 | 7/2005 | Tasch et al. | |
| 2004/0259690 A1 * | 12/2004 | Frykman et al. | 482/8 |
| 2009/0080709 A1 * | 3/2009 | Rowe et al. | 382/115 |

OTHER PUBLICATIONS

Clarke, KA et al. "Ground reaction force and spatiotemporal measurements of the gait of the mouse". Behavior Research Methods, Instruments, & Computers. 2001, 33(3), p. 422-426.*

* cited by examiner

*Primary Examiner* — Michael C Stout
(74) *Attorney, Agent, or Firm* — Whitham, Curtis & Cook, P.C.

(57) ABSTRACT

A system and method for measuring and analyzing locomotion is provided. The system may include a gait analysis apparatus that is configured to provide multi-dimensional measurements of the gait of an individual as the individual traverses the apparatus. The multiple dimensions may include force, space, time, and frequency. The gait analysis apparatus may be configured to provide a gait measurement processing device with the multi-dimensional measurements. Based on the multi-dimensional measurements, the gait measurement processing device may, for example, diagnose the test subject with a particular NM disease and/or injury, monitor progression of the particular NM disease and/or injury over time, and determine which measurements may be used as biomarkers to identify the particular NM disease and/or injury.

33 Claims, 12 Drawing Sheets

DIAGNOSIS SYSTEM AND METHOD

CROSS-REFERENCE TO RELATED APPLICATIONS

This application claims priority and benefit under 35 U.S.C. §119(e) to U.S. Provisional Patent Application No. 61/154,893, entitled "Gait Analysis of Locomotory Impairment in Rats Before and After Neuromuscular Injury", filed on Feb. 24, 2009. The content of that application is incorporated herein in its entirety by reference.

BACKGROUND OF THE INVENTION

An individual (i.e., human or animal) suffering from disease or injury may experience Neuromuscular (NM) dysfunction. For example, a disease such as Amyotrophic Lateral Sclerosis (ALS; commonly, "Lou Gehrig's disease"), Parkinson's disease, or other disease may impair or otherwise alter the gait (e.g., locomotion) of an individual suffering from the disease. Oftentimes, early diagnosis of such disease or injury can be useful in early treatment therapies. Furthermore, monitoring disease progression by observing changes to the gait of the individual over time, for example, may provide data that may be used to evaluate treatments such as drug therapies, physical therapies, and others.

However, existing systems have some limitations in their ability diagnosis and/or monitoring of NM disease or injury. In particular, diagnosis of such diseases may be challenging because, for example, the epidemiology of certain NM diseases or injury may not be known. Furthermore, monitoring changes to the gait of the individual may not be possible from a visual inspection of the individual's gait. In addition, existing gait analysis systems do not adequately identify various parameters related to the gait of the individual that may be used to diagnose and monitor NM disease or injury. These and other drawbacks exist.

SUMMARY

According to various embodiments of the disclosure, the system may include a gait analysis apparatus that is configured to provide multi-dimensional measurements of the gait of an individual as the individual (hereinafter "test subject") traverses the apparatus. The gait analysis apparatus may be configured to provide a gait measurement processing device with the multi-dimensional measurements. Based on the multi-dimensional measurements, the gait measurement processing device may, for example, diagnose the test subject with a particular NM disease and/or injury, monitor progression of the particular NM disease and/or injury over time, and/or determine which measurements may be used as biomarkers to identify the particular NM disease and/or injury.

Various other objects, features, and advantages of the invention will be apparent through the detailed description of the preferred embodiments and the drawings attached hereto. It is also to be understood that both the foregoing general description and the following detailed description are exemplary and not restrictive of the scope of the invention.

DETAILED DESCRIPTION OF THE DISCLOSURE

Figure 1:
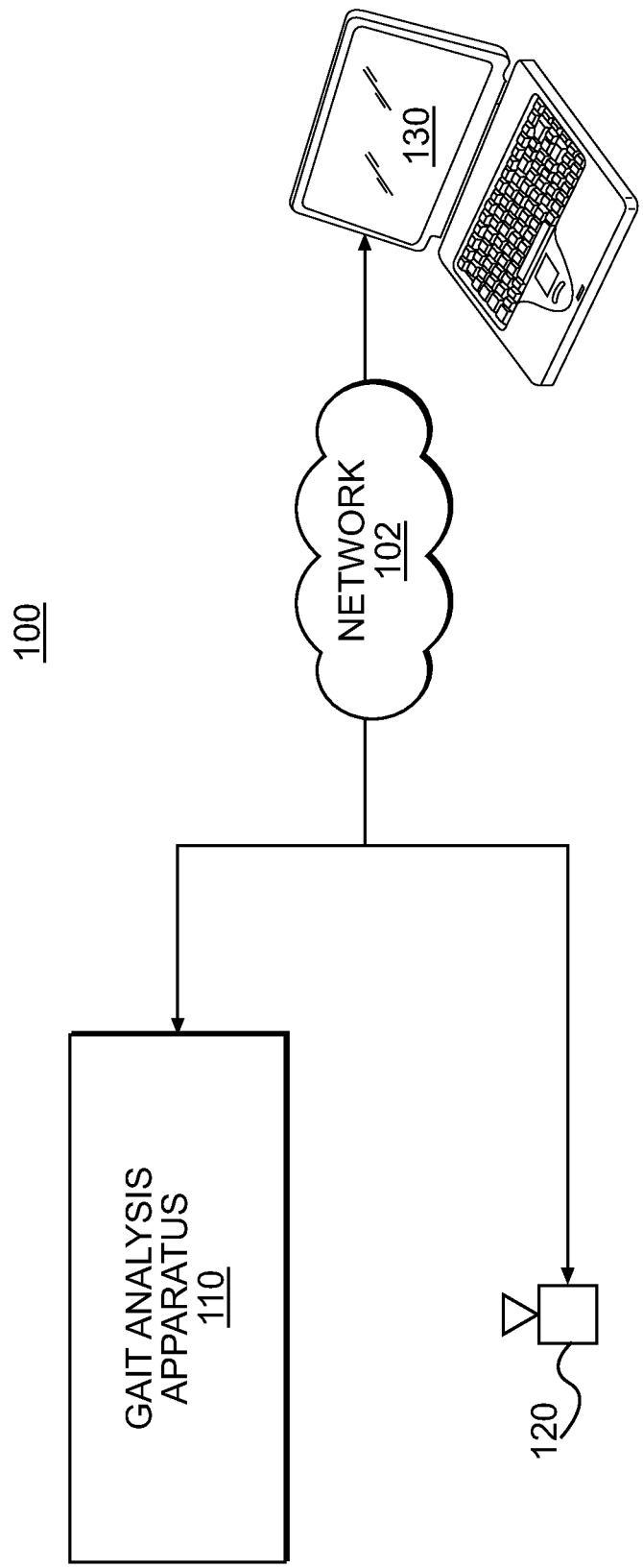
FIG. 1 is a block diagram illustrating an example system of gait analysis according to an embodiment of the disclosure.

According to various embodiments of the disclosure, the system may include a gait analysis apparatus that is configured to provide multi-dimensional measurements of the gait of an individual (i.e., human or animal) as the individual (hereinafter "test subject") traverses the apparatus. The multiple dimensions may include force, time, magnitude, frequency and space. The gait analysis apparatus may be configured to provide a gait measurement processing device with the multi-dimensional measurements. Based on the multi-dimensional measurements, the gait measurement processing device may, for example, diagnose the test subject with a particular NM disease and/or injury, monitor progression of the particular NM disease and/or injury over time, and determine which measurements may be used as biomarkers to identify the particular NM disease and/or injury.

In one embodiment, the apparatus may include a sensor region that measures one or more loads (or forces) imposed upon the sensor region. The sensor region may include at least one load sensor module, which may consist of a single multidimensional loads sensor or otherwise be coupled to a plurality of load sensors that are each configured to provide measurements of loads (i.e., forces) placed upon the sensor region (i.e., a load imposed upon a load sensor coupled to the sensor region) in one or more directions relative to the gait analysis apparatus as the test subject traverses the apparatus. In particular, a sensor may indicate a vertical load imposed upon a load sensor, a lateral load imposed upon a load sensor, and/or a for-aft load imposed upon a load sensor. In this manner, the sensor region may provide measurements of the various loads imposed upon the gait analysis apparatus as it is being traversed by the test subject.

According to a particular embodiment, the gait analysis apparatus may also measure stride and stance times of the test subject. Thus, each sensor may be specialized to provide measurements of a particular load imposed upon the sensor region in a particular direction.

By using measurements of loads across multiple dimensions, stride length, and/or stance time, the apparatus may provide robust measurements of the gait of the test subject that may be used for diagnosis, monitoring, and identification of biomarkers for NM disease and/or injury.

In particular for four legged test subjects, the inability to control the test subject's speed when traversing the apparatus generates unwanted variances between testing trials. Naturally, a test subject changes its speed when traversing in a given direction. However, the change of speeds varies simultaneously with respect to left and right limbs of the test subject. Thus, a two or more floor plate system offsets the discrepancies caused by the inability to control the traversing speed of four-legged test subjects and produces robust measurement of the test subject's gait. According to various embodiments of the disclosure, the sensor region may include two or more floor plates that are positioned adjacently to one another. In a particular embodiment, the two or more floor plates are configured to move independently of one another. In this manner, one floor plate may provide measurements of one side of the test subject (e.g., the left limb(s) of the test subject) while another floor plate may provide measurements of another side of the test subject (e.g., the right limb(s) of the test subject).

To ensure a test subject traverses the apparatus properly, impediments to animal movements may be provided. One impediment may be to restrict the width of the sensor region in accordance with the size of the test subject, such that the left and right limbs are forced to be properly place on the two or more floor plates. Other possible impediments that may be implemented are disclosed in U.S. Pat. No. 6,699,207, entitled "Method and Apparatus for Detecting Lameness in Animals," and which is fully and expressly incorporated herein by reference; possible impediments may include side railings and a partition or divider. The side railings constrain the test subject's lateral movement to thereby force the test subject to walk over the sensor region. In addition, a partition or divider extending along the adjoining edges of the adjacent floor plates may be used to address the uncommon problem of limb-crossover. The partition or divider prompts the test subject to place left limbs on one floor plate and to set right limbs on another floor plate. As discussed in U.S. Pat. No. 6,699,207, a partition or divider is not required because limb-crossover is uncommon and may be rectified by additional runs of the test subject through the apparatus and/or by corrective data analysis methods (e.g., manual manipulation of the data).

According to various embodiments of the disclosure, the floor plates may be configured such that one floor plate includes at least one load sensor module and the other floor plate(s) lack(s) any load sensor capabilities. In other words, only one of the two or more plates, which construct the sensor region, is configured to provide measurements of loads (i.e., forces) placed upon the sensor region (i.e., a load imposed upon a load sensor coupled to the sensor region) in one or more directions relative to the gait analysis apparatus as the test subject traverses the apparatus. The test subject's gait analysis is still obtainable by traversing the sensor region two or more times. The test subject may traverse the apparatus in one direction to measure one side of the test subject's limbs; and, then, test subject may traverse the apparatus in the opposite direction to measure the second side of the test subject's limbs. In this manner, both the left and right sides of the test subject will contact the floor plate that includes at least one load sensor module.

According to various embodiments of the disclosure, the system may include a limb placement detection system, which may be used to distinguish a measured load for a test subject's one or more limb(s). The limb placement detection system may include a plurality of light-emitting diodes (LEDs) and an image capture device.

According to various embodiments of the disclosure, the plurality of LEDs may be dispersed along the surface of the sensor region. The plurality of LEDs illustrate a precise location where a test subject's specific limb generated a force by illuminating the specific location on the sensor region. The LED illuminated area is captured by the image capture device. The image capture device is configured to provide one or more images of the test subject as the test subject traverses the gait analysis apparatus. The images may be used to enhance gait analysis of the test subject. For example, in conjunction with the plurality of LEDs, the images may be used to manually and/or automatically associate a measured load to one or more limb(s) of the test subject that generated the load. In other words, the images may be used to identify which limb of the test subject generated the particular measured load. In this manner, the system may analyze measurements of not only the overall gait of the test subject but it may also analyze measurements to a granularity of each individual limb of the test subject. According to various embodiments of the disclosure, the plurality of LEDs and the image capture device may incorporate infrared capabilities. The use of infrared capabilities for the limb placement detection system generates a more accurate coordination of test subject's individual limb positioning.

However, correlation of a measured load to specific limb(s) is not limited to a limb placement detection system that includes a image capture device and a plurality of LEDs. For four-legged animals, particularly rats, the dominant test subject used in medical testing, the rats' tail may interfere with the forces generated from the limbs. Thus, a limb placement detection system is advantageous to correlate the loads generated by a test subject to a specific limb. However, for test subjects without such interference issues, a limb placement detection system may be unnecessary and measured loads can be designated to a specific limb without the use of a plurality of LEDs and/or an image capture device features.

According to various embodiments of the disclosure, the image capture device may be placed underneath the gait analysis apparatus such that the sensor region is disposed between the image capture device and the test subject. As such, the sensor region may be constructed using a material that is transparent to the image capture device. In a particular embodiment, the image capture device is a video camera and the sensor region is constructed using a transparent material such as, for example, plexi-glass.

According to various embodiments of the disclosure, the system may include a processing device configured to receive multi-dimensional measurements of an individual (such as the test subject discussed above). The system may receive the multi-dimensional measurements from the apparatus described herein or other measurement apparatus. Based on the multi-dimensional measurements, the processing device may generate locomotion parameters (LPs) that each indicates empirical observation of a particular aspect of the gait of the test subject. For example, an LP may indicate a vertical force imposed upon a load sensor, a lateral load imposed upon a load sensor, and/or a for-aft load imposed upon a load sensor.

According to various embodiments of the disclosure, the processing device may perform statistical analyses on the LPs. An analyses may include a statistical transformation, such as a non-optimal, optimal, identity, or spline. An identity transformation is a statistical analysis in which no mathematical transformation is executed. In a particular embodiment of the disclosure, a spline transformation was utilized to analyze the LPs for ALS, Parkinson, and muscular injury. While execution of a statistical transformation may improve the predictive accuracy of the device, the processing device is not limited to its performance.

FIG. 1 is a block diagram illustrating an example system 100 of gait analysis according to an embodiment of the disclosure. According to various embodiments of the disclosure, system 100 may include a gait analysis apparatus 110, an image capture device 120, and a gait measurement processing device 130 (GMPD 130). Gait analysis apparatus 110 (GAA 110) may be an apparatus through which the test subject traverses. As GAA 110 is traversed by the test subject, GAA 110 may measure various loads, or forces, resulting from the traversal. According to various embodiments of the disclosure, image capture device 120 may generate image capture data of the test subject such that the one or more images may be associated with the measured loads. Image capture device 120 may be, for example, a video camera, an infrared imaging device, and/or others.

GAA 110 and image capture device 120 may be communicably coupled via network 102 to GMPD 130 such that the load measurements and/or the image capture data may be provided to GMPD 130 for analysis. GMPD 130 may analyze the received load measurements from GAA 110 or other apparatus and/or image capture data from image capture device 120 to, for example, diagnose the test subject with a NM disease and/or injury, monitor the test subject, and determine biomarkers for determining which gait measurements provided by GAA 110 (or other apparatus) may be used to predict a particular NM disease and/or injury.

Although illustrated as being coupled to GMPD 130 via network 102, GAA 110 and image capture device 120 may be coupled to GMPD 130 via a direct connection known in the art such as a USB connection, among others.

Figure 2:
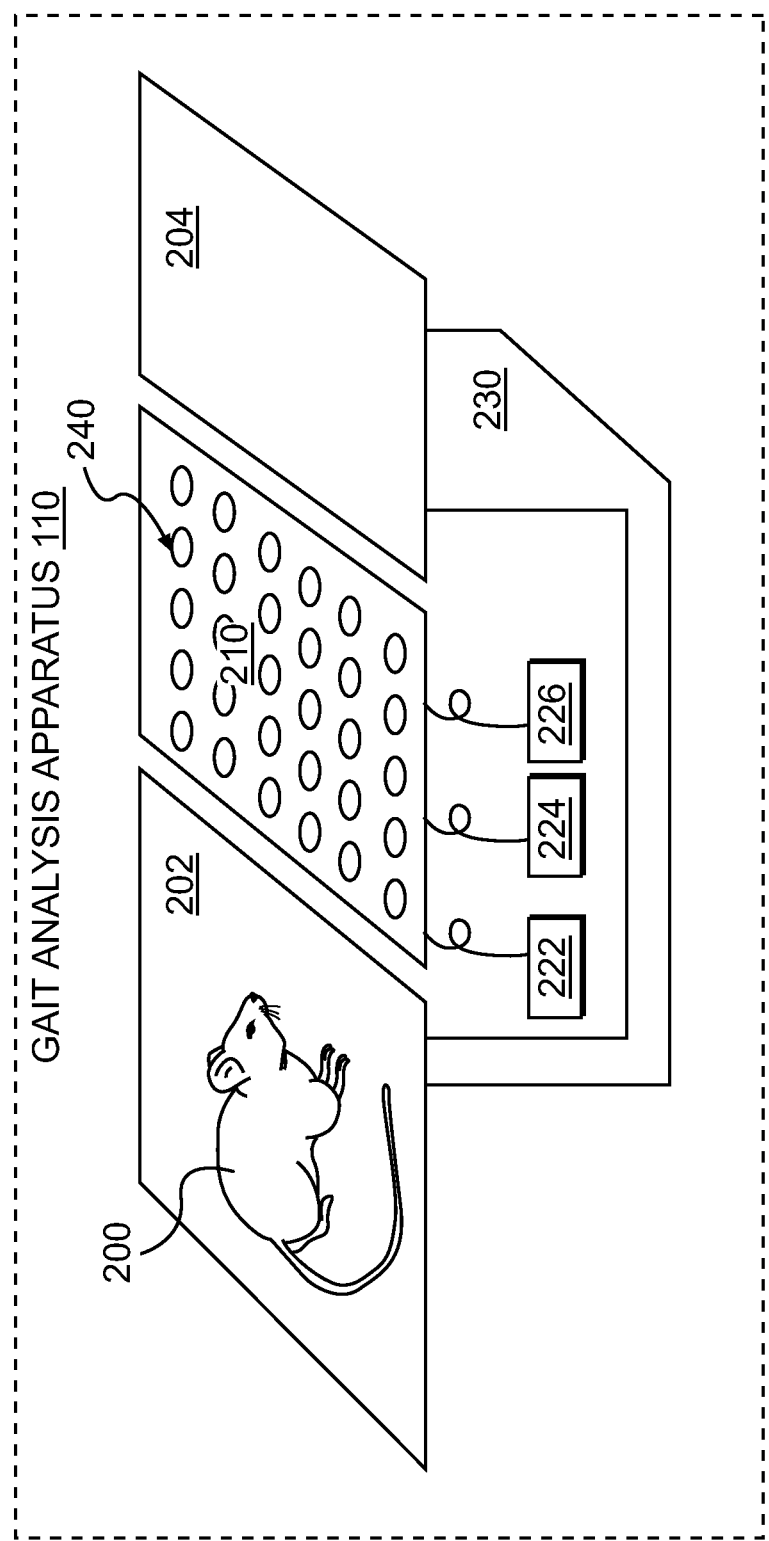
FIG. 2 is a perspective view of a gait analysis apparatus with a test subject according to an embodiment of the disclosure.

FIG. 2 is a perspective view of GAA 110 with test subject 200 according to an embodiment of the disclosure. Through various components, GAA 110 may measure various loads placed upon GAA 110 as test subject 200 traverses GAA 110 such that the measured loads may be processed for, among other things, diagnosing the test subject, monitoring measurements of the gait of the test subject over time, and determining one or more biomarkers that indicate a diagnosis of a particular disease.

For example, the GAA 110 may include, among other things, an entry region 202, an exit region 204, and a sensor region 210, at least some of which may be coupled to frame assembly 230. As illustrated in FIG. 2, test subject 200 may enter GAA 110 via entry region 202, traverse GAA 110 through sensor region 210, and exit GAA 110 via exit region 204. According to various embodiments of the disclosure, entry region 202, exit region 204, and sensor region 210 may each be substantially planar. Moreover, even though entry region 202, exit region 204, and sensor region 210 are illustrated as substantially rectangular, each may be formed into any other shape that would facilitate the measurement of the test subject's gait.

According to various embodiments of the disclosure, as test subject 200 traverses GAA 110 from entry region 202 through sensor region 210 and exits GAA 110 via exit region 204, sensor region 210 may be configured to measure loads in multiple dimensions exerted by test subject 200. For example, sensor region 210 may include or otherwise be coupled to at least one load sensor module. A load sensor module may incorporate at least one multidimensional load sensor (not shown; wherein a single multidimensional load sensor is capable of measuring vertical, for-aft, and lateral forces), or at least one vertical load sensor 222, at least one for-aft load sensor 224, and at least one lateral load sensor 226 (collectively, "load sensors 222, 224, and 226").

Vertical load sensor 222, for-aft load sensor 224, and lateral load sensor 226 may provide one or more measurements of vertical (or up-down), for-aft (or front-back), and lateral (or side-to-side) loads, respectively. In other words, in a hypothetical X-Y-Z coordinate system (not shown) where the test subject traverses GAA 110 along substantially the Y-axis (horizontally), vertical load sensor 222 may measure vertical (up-down along the Z-axis) loads, for-aft sensor 224 may measure for-aft (front-back along the Y-axis) loads in directions pointing to and from entry region 202 and exit region 204, and lateral load sensor 226 may measure lateral (side-to-side along the X-axis) loads. In this manner, using load sensors 222, 224, and 226, and/or at least one multidimensional load sensor, sensor region 210 may provide measurements of various loads imposed upon the gait analysis apparatus as it is being traversed by test subject 200.

The load sensor module may measure a plurality of respective vibrations (i.e., vertical, for-aft, and/or lateral) as a dimension of force (e.g., pound, Newton, etc.) and as a function of time (e.g., seconds). For example, load sensors 222, 224, and 226 may measure and provide a plurality of vibrations imposed upon load sensors 222, 224, and 226. In dimensions of force versus time, the plurality of vibrations have a undesirable degree of oscillations. The oscillations are not necessary to complete a diagnostic analysis for described methodology because, in comparison to the gait of a healthy limb, the gait an unhealthy limb varies in measurement to a degree of magnitude.

Figure 9:
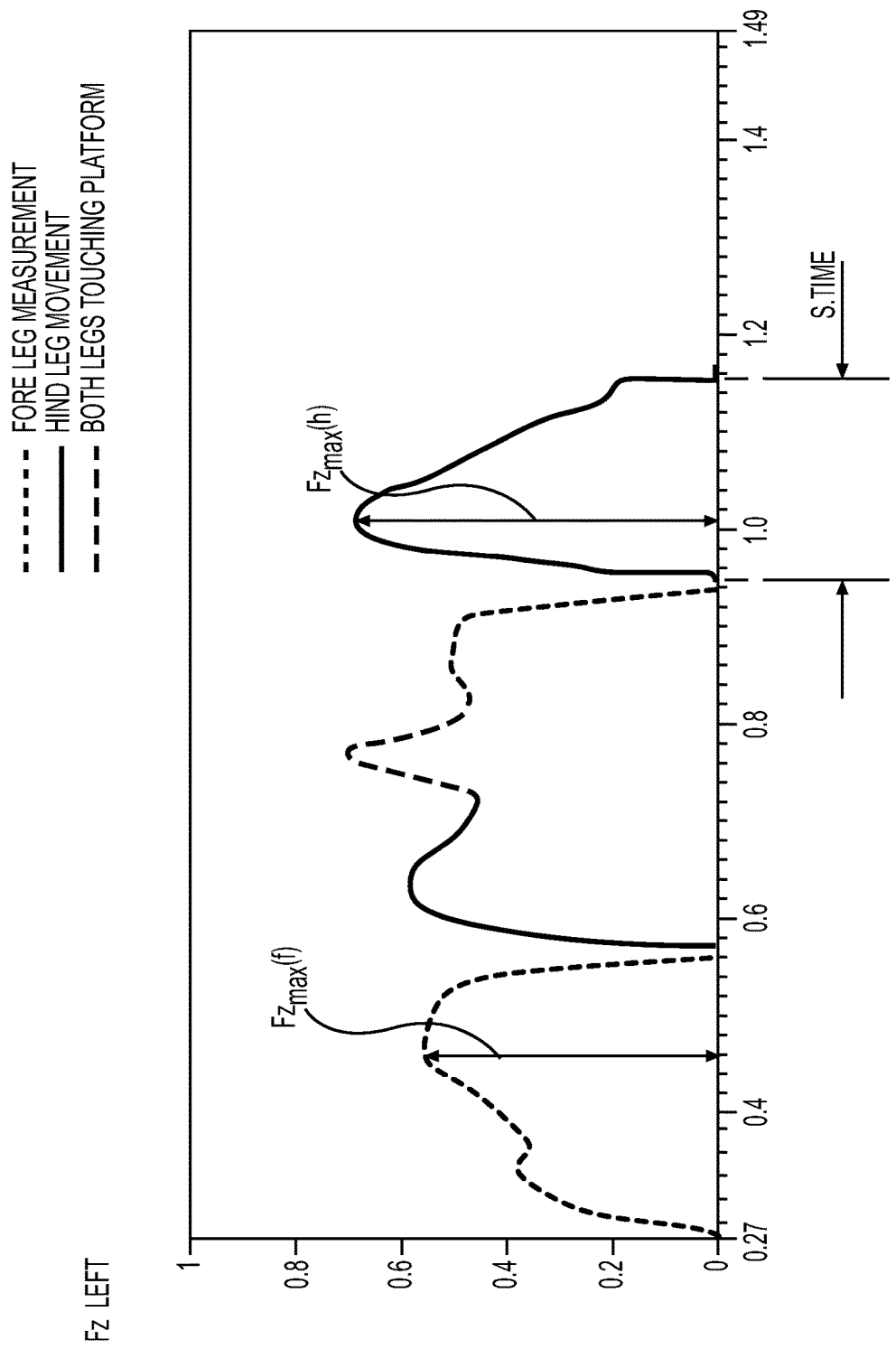
FIG. 9 is a two-dimensional graph illustrating load signatures of limbs from a first side of a test subject according to an embodiment of the disclosure.
Figure 10:
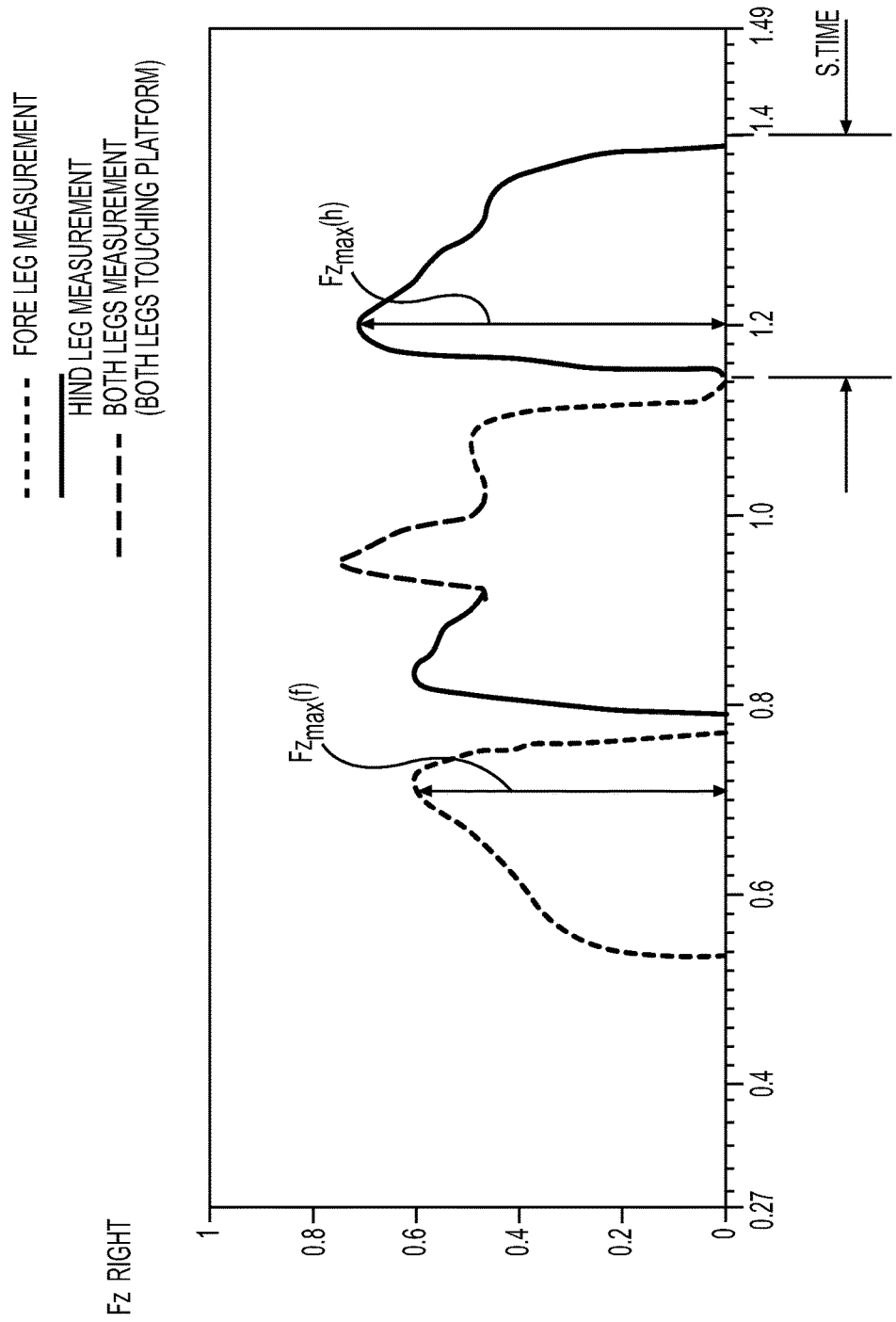
FIG. 10 is a two-dimensional graph illustrating load signatures of limbs from a second side of a test subject according to an embodiment of the disclosure.

As described in U.S. Pat. No. 6,699,207, the vibrations generated by the load sensor module may be normalized with respect to body weight and/or mass. According to various embodiments of the disclosure, the plurality of vibrations may be normalized, but not limited to, use of a Fourier transformation, such that the plurality of vibrations are recalibrated as functions of magnitude (non-dimensional) versus frequency (e.g., 1/seconds). The normalization of the plurality of vibrations reveals the magnitude of the force generated by a limb at the dominant frequency. For a graphical representation of the normalization of the generated forces, FIGS. 9 and 10 illustrate a plot of a generated load expressed as function of magnitude (non-dimensional) versus frequency (1/seconds). The elimination of adverse oscillation variances allows comparisons among different test subjects and symmetry variable may be used to compare left to right limbs of the test subject.

According to various embodiments of the disclosure, the apparatus may also measure stride length and stance time of the test subject. For example, stride length may measure a length of the stride of a limb of test subject 200. The stride length may be determined based on a difference between two consecutive contact positions with sensor region 210 as indicated by load sensor data and/or image capture data. The stance time may be a duration in which one or more of load sensors 222, 224, and 226 detects a load from a limb of test subject 200.

By using measurements of loads across multiple dimensions, stride length, and/or stance time, GAA 110 may provide robust measurements of the gait of the test subject 200 that may be used for diagnosis, monitoring, and identification of biomarkers for NM disease and/or injury. The measurements necessary to acquire for diagnosis, monitoring, and identification of biomarkers for NM disease and/or injury depends on the particular disease under consideration. For example, with respect to Parkinson's disease, the analysis of the gait of the test subject is not required in the vertical direction. Thus, a vertical load sensor and/or vertical force measurement by a multidimensional load sensor is not necessary because lateral and for-aft sensors and/or lateral and for-aft force measurements would suffice.

According to various embodiments of the disclosure, system 100 may include a limb placement detection system, consisting of an image capture device 120 and/or a plurality of LEDs 240 dispersed on the surface of sensor region 210, that is configured to provide one or more image data of test subject 200 as test subject 200 traverses GAA 110. The images may be used to enhance gait analysis of the test subject, particularly for test subjects that may easily interfere with the forces generated by the test subject's limb(s). For example, the images may be used to manually and/or automatically associate a measured load to one or more limb(s) of the test subject that generated the load. In other words, the images may be used to identify which limb of the test subject generated the particular measured load. In this manner, the system may analyze measurements of not only the overall gait of the test subject but also the analyze measurements to a granularity of each individual limb of the test subject. The same association of load to limb is feasible without a image capturing limb placement detection system for test subjects who do not present limb interference issues.

According to various embodiments of the disclosure, image capture device 120 may be placed underneath the GAA 110 such that the sensor region 210 is disposed between image capture device 120 and test subject 200. As such, sensor region 210 may be constructed using a material that is transparent to image capture device 120. In a particular embodiment, image capture device 120 is a video camera and sensor region 210 is constructed using a transparent material such as, for example, plexi-glass.

Figure 3:
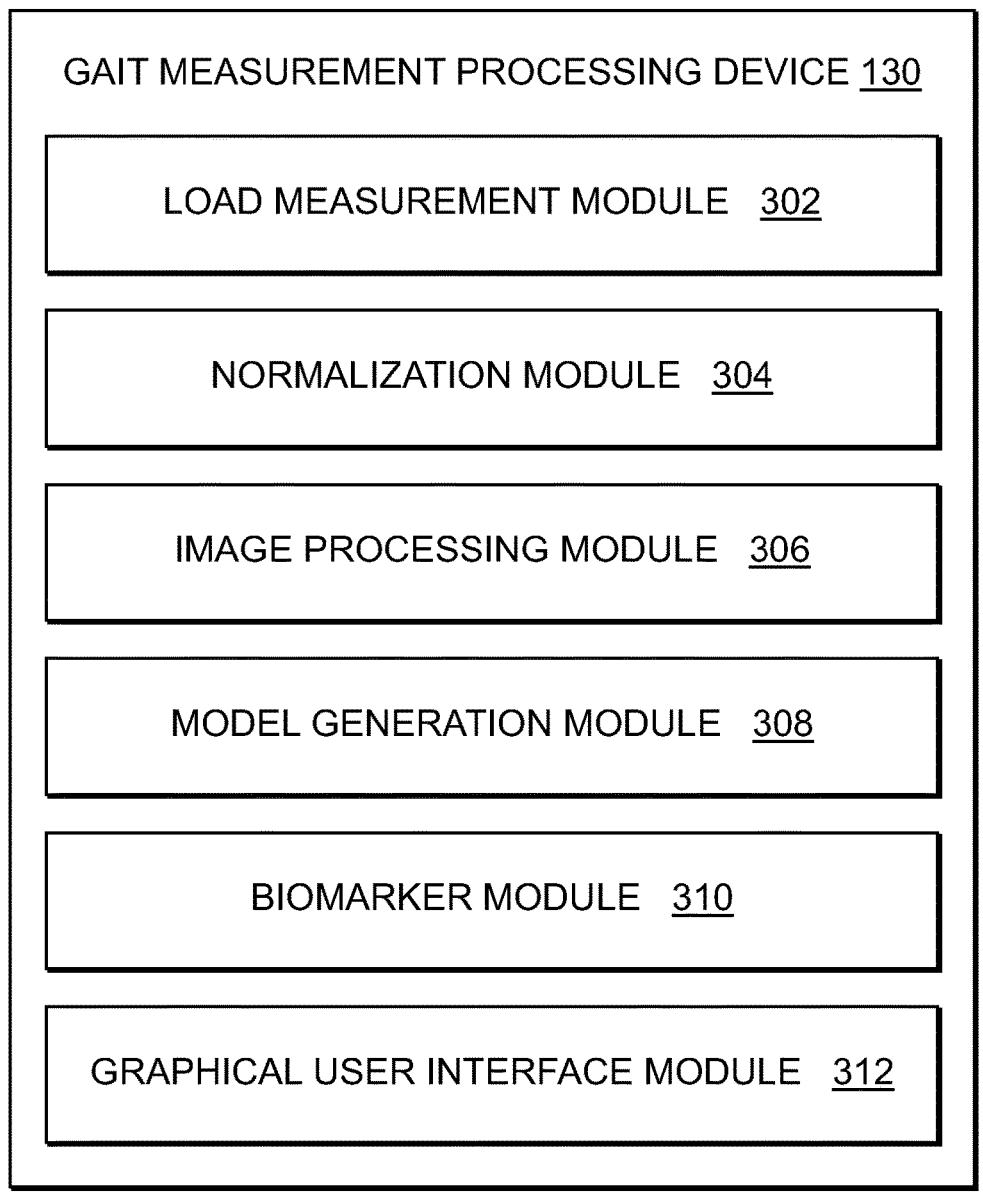
FIG. 3 is a block diagram illustrating an example of a gait measurement processing device according to an embodiment of the disclosure.

FIG. 3 is a block diagram illustrating an example of GMPD 130 according to an embodiment of the disclosure. Through various modules, GMPD 130 may receive multi-dimensional measurements of an individual, such as test subject 200, and analyze the measurements in order to, for example, diagnose test subject 200, monitor test subject 200, and/or determine biomarkers for a particular NM disease and/or injury. For example, GMPD 130 may include, among other things, a load measurement module 302, a normalization module 304, an image processing module 306, a model generation module 308, a biomarker module 310, and a graphical user interface (GUI) module 312.

According to various embodiments of the disclosure, load measurement module 302 may receive load measurements from GAA 110 or other measurement apparatus. For example, load measurement module 302 may receive load sensor data from each of load sensors 222, 224, and 226 for analysis or at least one multidimensional load sensor (not shown). Based on the received measurements, load measurement module 302 may generate one or more locomotion parameters (LPs) that each indicates empirical observation of a particular aspect of the gait of the test subject. For example, an LP may indicate a vertical load imposed upon vertical load sensor 222, a for-aft load imposed upon for-aft sensor 224, a lateral load imposed upon lateral load sensor 226, a stride length and/or a stance time. Table 1 illustrates non-limiting example LPs that may be generated.

TABLE 1

| No. | Variable | Units | Description |
|---|---|---|---|
| 1 | $Fz_{max}$ | Non-dimensional | Maximum value of the vertical load of a selected limb |
| 2 | Stance time | Seconds | Time duration that a selected limb is in contact with sensor region |
| 3 | $T\_Fz_{max}$ | Non-dimensional | Time of $Fz_{max}$ normalized by the stance time of a selected limb |
| 4 | $Fz_{mean}$ | Non-dimensional | Mean value of the vertical load of a selected limb |
| 5 | $Fz_\omega$ | 1/seconds | The Fourier transform of Fz summed over 50 Hz for a selected limb |
| 6 | Stride | Non-dimensional | Stride length of a selected limb calculated as the difference between two consecutive contact positions: the contact positions are normalized by the sensor region length. |
| 7 | $Fy_{max}$ | Non-dimensional | Maximum value of the for-aft load of a selected limb |
| 8 | $T\_Fy_{max}$ | Non-dimensional | Time of $Fy_{max}$ divided by Stance time |
| 9 | $Fy_{min}$ | Non-dimensional | Minimum value of the for-aft load of a selected limb |
| 10 | $T\_Fy_{min}$ | Non-dimensional | Time of $Fy_{min}$ divided by Stance time |
| 11 | $Fy_{mean}$ | Non-dimensional | The average value of the for-aft load of a selected limb |
| 12 | $Fy_\omega$ | 1/seconds | The Fourier transform of Fy summed over the first 50 Hz of a selected limb |
| 13 | $Fx_{max}$ | Non-dimensional | Maximum value of the lateral load of a selected limb |
| 14 | $Fx_{min}$ | Non-dimensional | Minimum value of the lateral load of a selected limb |
| 15 | $Fx_{mean}$ | Non-dimensional | The average value of the lateral load of a selected limb |

TABLE 1-continued

| No. | Variable | Units | Description |
|---|---|---|---|
| 16 | FyP | Non-dimensional | The mean value of the propelling (positive) for-aft load of a selected limb |
| 17 | FyB | Non-dimensional | The mean value of the braking (negative) for-aft load of a selected limb |
| 18 | NP | Non-dimensional | The number of samples in which the for-aft load is propelling (positive load) |
| 19 | NB | Non-dimensional | The number of samples in which the for-aft load is braking (negative load) |
| 20 | NPB | Non-dimensional | The number of times in which the for-aft load switches from braking to propelling and vice versa |
| 21 | $Sym\_Fx_{min}$ | Non-dimensional | Symmetry of $Fx_{min}$ |
| 22 | $Sym\_T\_Fy_{max}$ | Non-dimensional | Symmetry of $T\_Fy_{max}$ |
| 23 | $Sym\_Fx_{max}$ | Non-dimensional | Symmetry of $Fx_{max}$ |
| 24 | Sym_Stance Time | Non-dimensional | Symmetry of Stance Time |
| 25 | $Sym\_T\_Fz_{max}$ | Non-dimensional | Symmetry of $T\_Fz_{max}$ |
| 26 | $Sym\_Fy_{max}$ | Non-dimensional | Symmetry of $Fy_{max}$ |
| 27 | $Sym\_Fz_{mean}$ | Non-dimensional | Symmetry of $Fz_{mean}$ |
| 28 | $Sym\_Fz_{max}$ | Non-dimensional | Symmetry of $Fz_{max}$ |
| 29 | $Sym\_T\_Fy_{min}$ | Non-dimensional | Symmetry of $Fy_{min}$ |
| 30 | $Sym\_Fy_{mean}$ | Non-dimensional | Symmetry of $Fy_{mean}$ |
| 31 | $Sym\_Fz_\omega$ | Non-dimensional | Symmetry of $Fz_\omega$ |
| 32 | $Sym\_Fx_{mean}$ | Non-dimensional | Symmetry of $Fx_{mean}$ |
| 33 | $Sym\_Fy_{min}$ | Non-dimensional | Symmetry of $Fy_{min}$ |
| 34 | Sym_Stride | Non-dimensional | Symmetry of Stride |
| 35 | $Sym\_Fy\omega$ | Non-dimensional | Symmetry of $Fy_\omega$ |

According to various embodiments of the disclosure, GMPD 130 may use normalization module 304 to normalize measurements. For example, load measurements from load sensors 222, 224, and 226 may each be normalized according to the weight or mass of the test subject in order to account for variability of weights of test subjects. Normalization module 304 may also normalize distance measurements, such as stride length, according to the length of sensor region 210. In this manner, variability of weight, size, etc., of test subjects may be normalized as appropriate. As described above in regards to the transformation of generated vibrations of test subject's limbs, the normalization module 304 may execute the Fourier method, as disclosed in U.S. Pat. No. 6,699,207, to transform the forces as a function (e.g., pound, Newton, etc.) of time (seconds) to a non-dimensional form of magnitude versus frequency (1/seconds).

According to various embodiments of the disclosure, GMPD 130 may use image processing module 306 to receive and process image capture data received from the limb placement detection system, specifically the image capture device 120 and the associated plurality of LEDs 240. Image capture data may be used to, among other things, measure the stride length of test subject 200 and associate a particular limb of test subject 200 with particular measurements from load sensors 222, 224, and 226, or at least one multidimensional load sensor. In other words, LPs may be generated that are specific for a particular limb of test subject 200. In this manner, by using image capture data, GMPD 130 may provide analysis of gait measurements for particular limbs of test subject 200. However, gait measurements for particular limbs of test subject 200 without limb obstruction concerns is not limited to processing module 306.

According to various embodiments of the disclosure, GMPD 130 may use model generation module 308 in order to generate one or more statistical models using one or more LPs. Model generation module 308 may analyze one or more LPs to determine which LPs may predict a diagnosis of a particular NM disease and/or injury. Furthermore, by identifying the LPs that predict diagnosis, model generation module 308 may determine biomarkers that identify the particular NM disease and/or injury (i.e., the biomarkers may be the LPs that predict the diagnosis).

For example, to determine which LPs predict the diagnosis, model generation module 308 may compare LPs associated with test subjects known to be healthy with corresponding LPs of test subjects known to have a particular NM disease and/or injury ("unhealthy test subjects"). In a particular embodiment of the disclosure, model generation module 308 may transform each LP of test subject 200 using a spline basis, a particular family of nonlinear transformations, described in L. L. Schumaker, Spline Functions: Basic Theory (3rd ed., Cambridge University Press 2007), which is incorporated by reference herein in its entirety. For example, a first plurality of measurements obtained by one of load sensors 222, 224, and 226 may be transformed.

Each LP (transformed or otherwise) may be analyzed by model generation module 308 to determine a misclassification rate for the LP. The misclassification rate may be generated by counting a number of unhealthy test subjects that have been incorrectly predicted to be healthy based on an analysis of each LP as compared to a number of unhealthy test subjects that have been correctly predicted to be unhealthy based on an analysis of each LP. For example, a control test subject (i.e., a healthy test subject) is tested a number of times to generate a model of the appropriate measurements of the LPs. After completion of a substantial sample, the generated model is applied to an unhealthy test subject (i.e., one induced with a NM dysfunction), who is tested a number of times. As the unhealthy test subject traverses the apparatus, the model generation module 308, in consideration of the model generated by the control test subject, determines the probability that the unhealthy test subject belongs to the healthy (i.e., control) group or to a different group.

A determination of 100% probability represents a healthy rat, and a finding of 0% probability signifies an unhealthy rat. For any percentage concluded in between 0% and 100%, the determination of health depends on the cut-off model generated by the model generation module 308. For example, the cut-off probability may be 30%, meaning that if the determination concludes a probability in the range of 30% to 100%, then the test subject is considered healthy. And, if the probability falls in the range of 0% to 30%, the test subject is deemed unhealthy. The advantage of such a system is that it provides an objective quantitative methodology to determine the health of a test subject. Therefore, by eliminating the inclusion of unreliable qualitative subjective means, the health of a test subject may be more accurately determined.

According to various embodiments of the disclosure, model generation module 308 may select one or more LPs to be used to generate a model. The model could be using linear regression, logistic regression, Neural Net, or any other modeling method. If logistic regression is used, then the model may take the form described by D. W. HOSMER & S. LEMESHAW, APPLIED LOGISTIC REGRESSION (John Wiley and Sons, Inc. 2000), which is incorporated by reference herein in its entirety. Accordingly, a non-limiting example of a logistic regression model may be mathematically expressed as:

$$\text{Probability (Test Subject} \in \text{``Unhealthy'')} = \frac{\exp(\beta_0 + \sum \beta_i \cdot LP_i)}{1 + \exp(\beta_0 + \sum \beta_i \cdot LP_i)}, \quad (1)$$

where $LP_i$ represents the selected one or more LPs, $\beta_0$ is the value at the intercept of logistic regression model on the probability axis, and $\beta_i$ is the ith coefficient of the logistic regression model and is estimated by appropriate statistical methods. As graphically represented in FIGS. 9 and 10, the probability calculated by equation (1) may be shown as the plot of the probability of test subject's heath as a function of selected LPs, depending of the disease being modeled. In addition, $LP_i$ may be replaced with $TLP_i$, which represents the transformed value of the selected one or more LPs.

According to a particular embodiment of the disclosure, a non-limiting example, illustrated in Table 2, compares the top seven performing LPs of a SOD1 rat (i.e., a unhealthy rat), which exhibits symptoms of ALS, and a control rat (i.e., a healthy rat). The fore and hind limbs for both the left and right sides of both rats are evaluated. In this particular example, the top seven performing LPs include FyB, $T\_Fy_{max}$, $Fy_{max}$, $Fz_\omega$, $FZ_{mean}$, $Fy_\omega$, and NP.

Therefore, the advantages of performing a probability analysis of the individual LPs to determine the health of a test subject is apparent.

One or more LPs may be selected based on misclassification rates. According to a particular embodiment of the disclosure, the top 7 LPs (having the lowest misclassification rates) may be selected for inclusion into the model. The foregoing is a non-limiting example. For example, any number of the top LPs may be selected and model generation module 308 may iteratively analyze various numbers of top LPs when generating the model. Furthermore, the LPs may be selected on the basis of a predefined threshold (e.g., LPs having misclassification rates below 30%, for example, may be selected for inclusion into the model).

Once generated, the model may be associated with a range of probabilities that particular test subjects are healthy or unhealthy. In this manner, biomarker module 310 may use the model to identify LPs (i.e., the top LPs used in the model) that may be used as biomarkers that identify the particular NM disease and/or injury. By doing so, GMPD 130 may compare one or more biomarkers of the particular disease and/or injury with corresponding LPs of the test subject 200 in order to diagnose test subject 200.

Furthermore, by providing a framework for analysis of LPs, GMPD 130 may be used to monitor a specific test subject 200 by comparing biomarkers of test subject 200 at various time intervals. For example, in order to monitor the efficacy of treatment therapies directed to treat a particular NM disease and/or injury, biomarkers associated with the particular NM disease and/or injury may be monitored at various time intervals. In other words, gait biomarkers of test subject 200 may be monitored over the course of one or more treatment therapies in order to monitor efficacy of the treatment therapies. In addition, as illustrated in Table 9, provided below, the recovery rate of locomotory impaired test subjects varies, depending on external factors, such as pain tolerance. Thus, GMPD 130 may be used to ascertain an appropriate time to cease treatment, upon an quantitative showing of complete recovery by the device.

Figure 8:
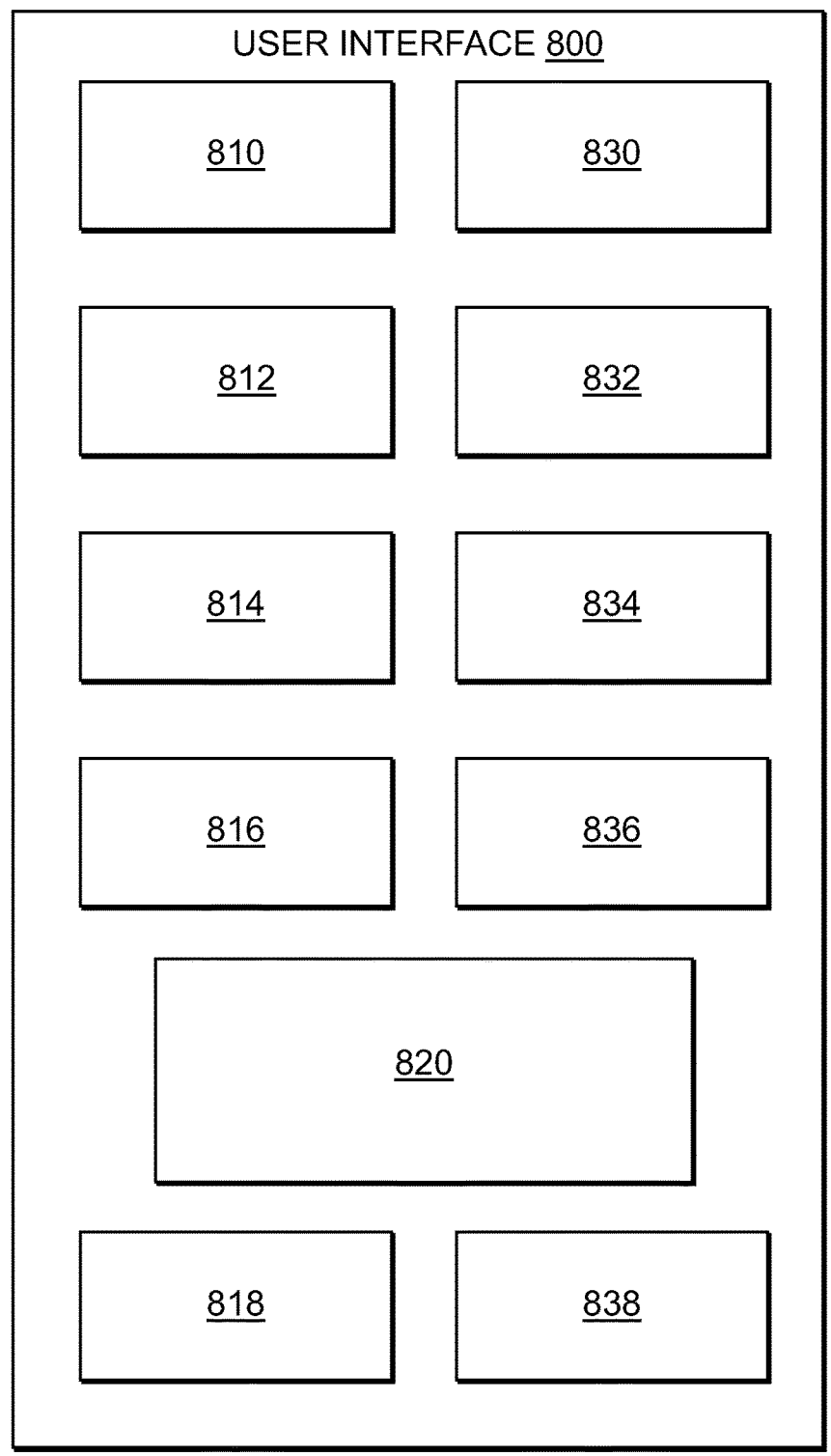
FIG. 8 is a screenshot illustrating a user interface displaying graphs of load signatures and image capture data according to an embodiment of the disclosure.

According to various embodiments of the disclosure, GUI module 312 may generate a user interface, such as an example user interface 800 described in FIG. 8. The user interface 800 may include a display of graphs of load signatures 810, 812, 814, 816, 818, 830, 832, 834, 836, and

TABLE 2

| LPs | Left Fore Limb | | Right Fore Limb | | Left Hind Limb | | Right Hind Limb | |
|---|---|---|---|---|---|---|---|---|
| | SOD1 | Control | SOD1 | Control | SOD1 | Control | SOD1 | Control |
| FyB | −0.0407 | −0.1936 | −0.0372 | −0.0440 | −0.1541 | −0.7466 | −0.2568 | −0.1794 |
| $T\_Fy_{max}$ | 0.9756 | 0.8710 | 0.9455 | 0.1786 | 0.8043 | 0.5172 | 0.3023 | 0.4571 |
| $Fy_{max}$ | 0.1784 | 0.1517 | 0.1913 | 0.3986 | 0.0940 | 0.0178 | 0.1318 | 0.3771 |
| $Fz_\omega$ | 0.3194 | 0.5326 | 0.4023 | 0.5280 | 0.5434 | 0.5194 | 0.4433 | 0.4605 |
| $Fz_{mean}$ | 0.2677 | 0.5288 | 0.2745 | 0.5260 | 0.5118 | 0.4221 | 0.3742 | 0.3918 |
| $Fy_\omega$ | 0.1074 | 0.2769 | 0.1352 | 0.2621 | 0.1839 | 0.0842 | 0.1065 | 0.2377 |
| NP | 21 | 5 | 33 | 6 | 17 | 22 | 26 | 23 |

As illustrated in Table 2, because the individual LP values vary arbitrarily when comparing the control and SOD1 rats, it is difficult to distinguish the unhealthy rat (i.e., SOD1) from the healthy rat (i.e., "Ctrl") based on the individual LP values. However, based on the LPs provided and by implementing a logistic regression model, as exemplified in equation (1), the probability the SOD1 rat was "unhealthy" (i.e., exhibited symptoms of ALS) was 99.991% and the probability the control rat was "unhealthy" was 0.0116%.

838 and/or image capture data 820 according to an embodiment of the disclosure. The load signatures and/or image capture data may include, but not limited to, graphical representations of the LPs disclosed in Table 1.

Figure 4:
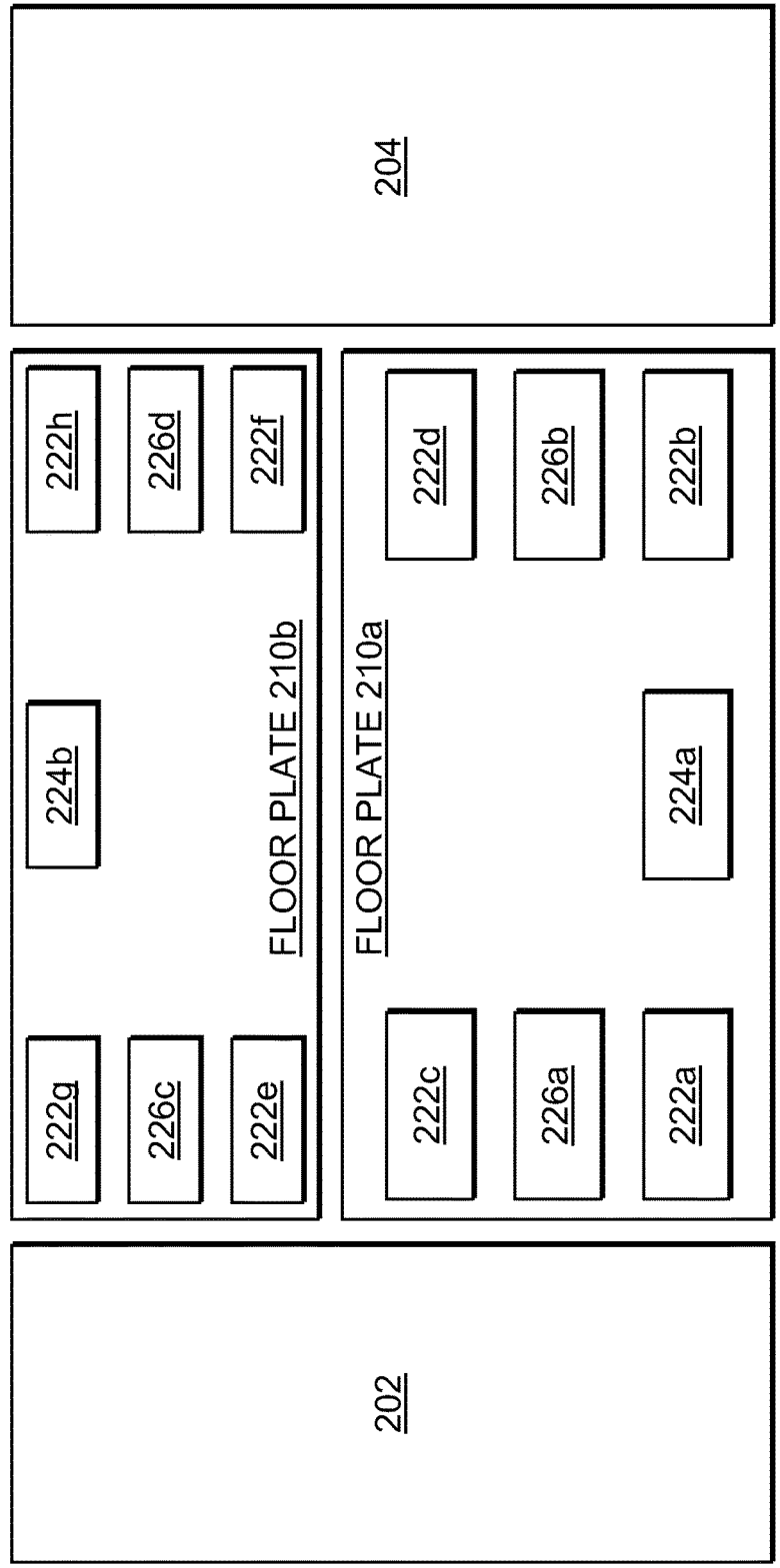
FIG. 4 is a plan view of example floor plates of a gait analysis apparatus illustrating orientations of various load sensors according to an embodiment of the disclosure.

FIG. 4 is a plan view of example floor plates 210a and 210b (collectively, "floor plates 210a, 210b") of gait analysis apparatus 110 illustrating orientations of various load sensors 222a, 222b, 222c, 222d, 222e, 222f, 222g, 222h, 224a, 224b, 226a, 226b, 226c, and 226d according to an embodiment of the disclosure. According to a particular embodiment of the disclosure as illustrated in FIG. 4, sensor region 210 includes a first floor plate 210a and a second floor plate 210b that are disposed adjacently to one another. The floor plates, 210a and 210b, may be constructed of a material that would encourage the test subject to traverse the sensor region. Thus, the floor plates may be substantially rigid, such that a test subject feels secure traversing along the sensor region. The first floor plate 210a and second floor plate 210b may be made of a rigid material, such as plastic (with incorporation of image capture device 120) or metal (without incorporation of image capture device 120). Moreover, natural flexibility of the floor plates' material should be minimized to reduce interference with the vibrations generated by test subject's limbs. One end of the first floor plate 210a and 210b may be mounted to either entry region 202 and/or frame assembly 230, and the opposite end may be coupled to exit region 204 and/or frame assembly 230. Furthermore, entry region 202 and exit region 204 may be independently mounted to frame assembly 230.

In this particular embodiment, test subject 200 (not shown) enters GAA 110 via entry region 202 and steps onto first floor plate 210a and/or second floor plate 210b, then exits GAA 110 via exit region 204. First floor plate 210a and second floor plate 210b may move independently of one another. As such, each may be associated with or be coupled to respective sensors. For example, first floor plate 210a may be coupled to: four vertical load sensors 222a, 222b, 222c, and 222d; one for-aft load sensor 224a, and two lateral load sensors 226a and 226b. Likewise, second floor plate 210b may be coupled to: four vertical load sensors 222e, 222f, 222g, and 222h; one for-aft load sensor 224b, and two lateral load sensors 226c and 226d. In this manner, floor plates 210a and 210b may be coupled to a total of 14 load sensors. In this manner, as test subject 200 traverses GAA 110, load measurements may be provided across multiple dimensions.

Figure 5:
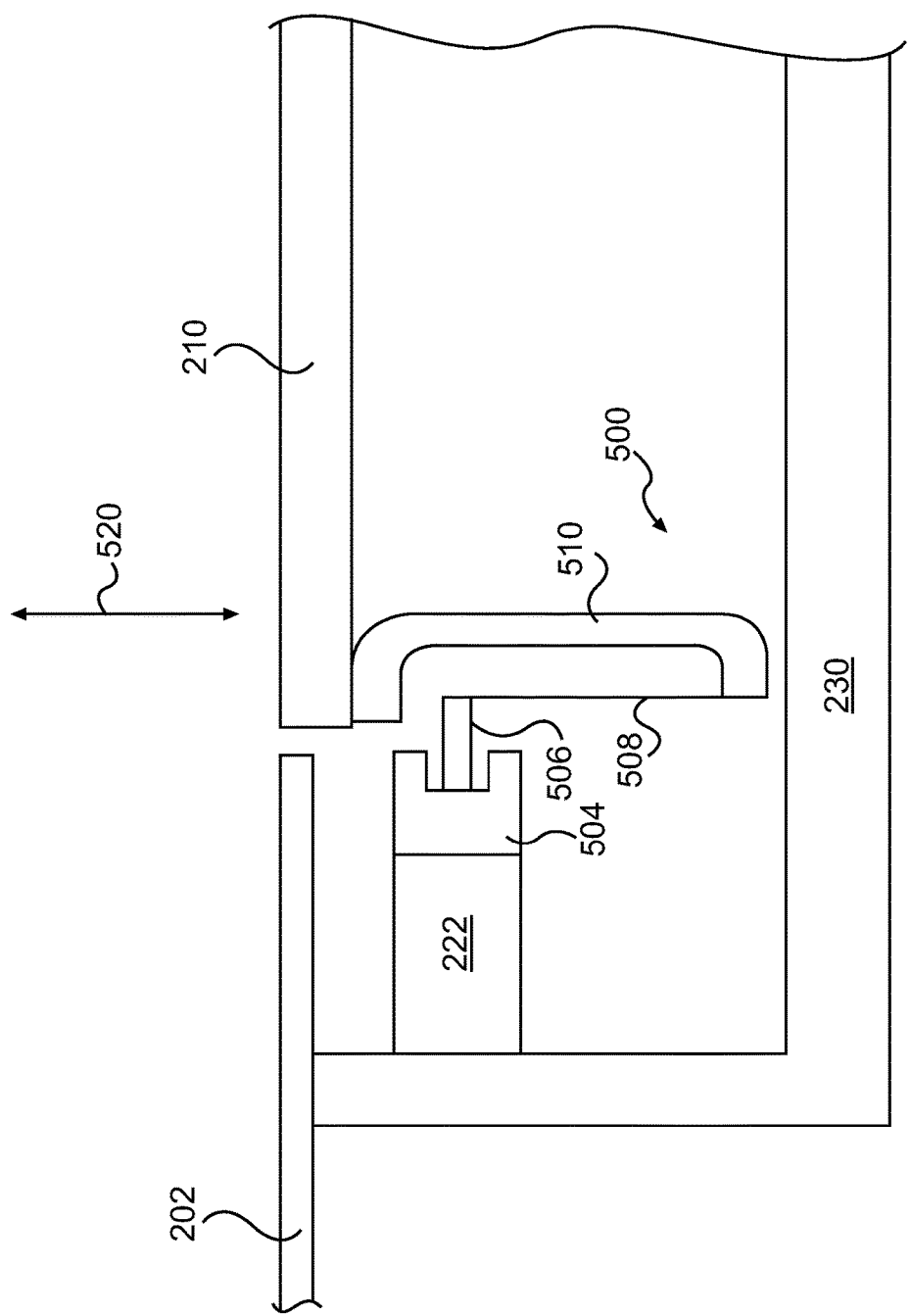
FIG. 5 is a plan view of an example vertical load assembly according to an embodiment of the disclosure.

FIG. 5 is a plan view of an example vertical load assembly 500 that includes a vertical load sensor 222 according to an embodiment of the disclosure. According to various embodiments of the disclosure, frame assembly 230 may be coupled to vertical load sensor 222. Vertical load sensor 222 may be coupled to z-bracket 504, which may be coupled to flexible link attachment nut 506. Flexible link attachment nut 506 may be coupled to flexible link 508, which may be, for example, a string, wire, rope, cable, chain, etc. The flexible link 508 may be composed of a material such as, for example, nylon, metal, natural fibers, or any other flexible material. The required degree of flexibility and strength for flexible link 508 depends on the forces being applied to the system by the test subject. Thus, for a test subject with a considerable mass, such as a horse or cow, a stronger flexible link, such as a chain, may be necessary. In comparison, for test subjects of lesser proportions, such as a rat, a nylon string may be sufficient. Flexible link 508 may be coupled to c-bracket 510, which may be coupled to sensor region 210 (i.e., 210a and/or 210b). Thus, according to the embodiment illustrated in FIG. 5, sensor region 210 (i.e., 210a and/or 210b) may be suspended by flexible link 508. A vertical load applied to sensor region 210 (i.e., 210a and/or 210b; such as when test subject 200 steps onto or off sensor region 210) in a direction illustrated by load direction 520 may cause c-bracket 510 to move in load direction 520. Movement of c-bracket 510 in load direction 520 causes flexible link 508 to exert a vertical load on flexible link attachment nut 506 in load direction 520, thereby causing vertical load sensor 222 to measure the vertical load applied in load direction 520.

Figure 6:
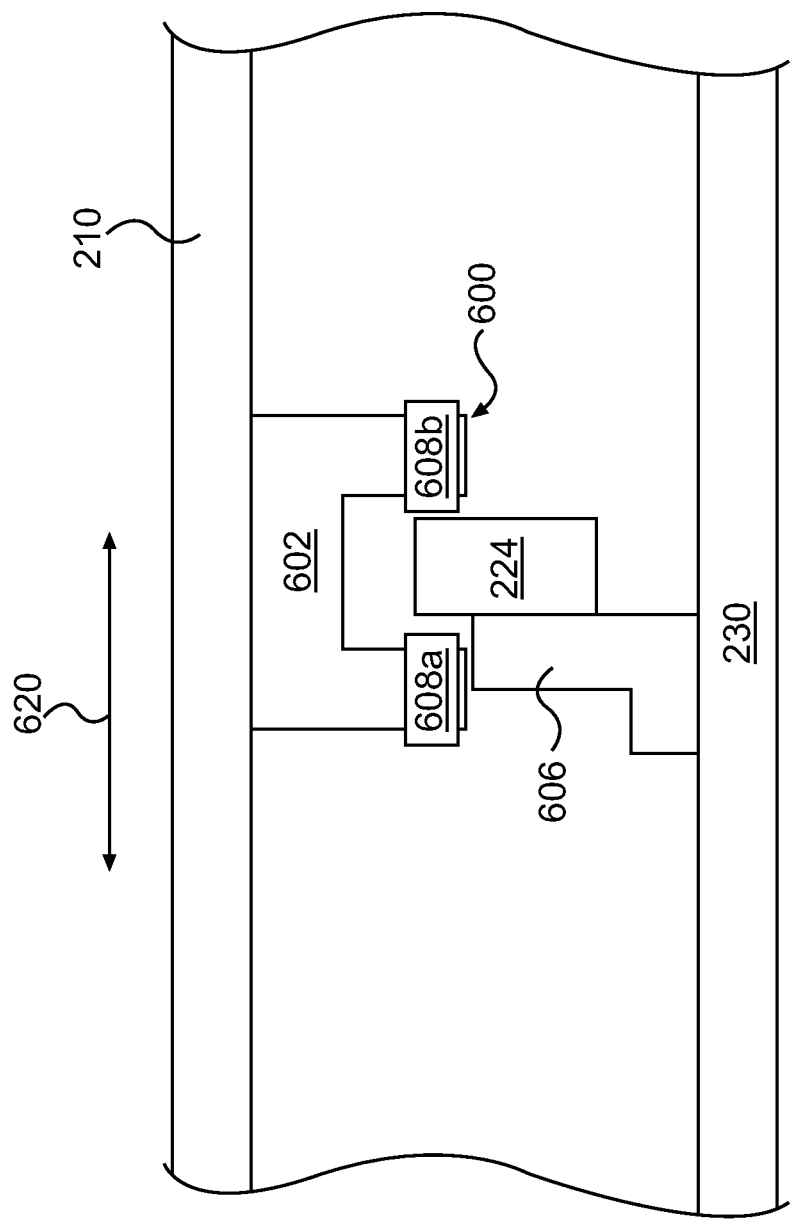
FIG. 6 is a plan view of an example for-aft load assembly according to an embodiment of the disclosure.

FIG. 6 is a plan view of an example for-aft load assembly 600 that includes for-aft sensor 224 according to an embodiment of the disclosure. According to various embodiments of the disclosure, frame assembly 230 may be coupled to for-aft sensor mount 606, which may be coupled to for-aft sensor 224. In other words, for-aft sensor mount 606 may mount for-aft sensor 224 to frame assembly 230. Set Screws 608a and 608b may be coupled to side bracket 602. The ends of each set screw 608a and 608b are arranged to limit the freedom of sensor region's 210 movement. Side bracket 602 may be coupled to sensor region 210 such that a for-aft load applied to sensor region 210 (such as when test subject 200 steps onto or off sensor region 210) in a direction illustrated by load direction arrow 620 may cause side bracket 602 to move in load direction 620. Movement of side bracket 602 may cause for-aft sensor 224 to measure the for-aft load applied in load direction 620.

Figure 7:
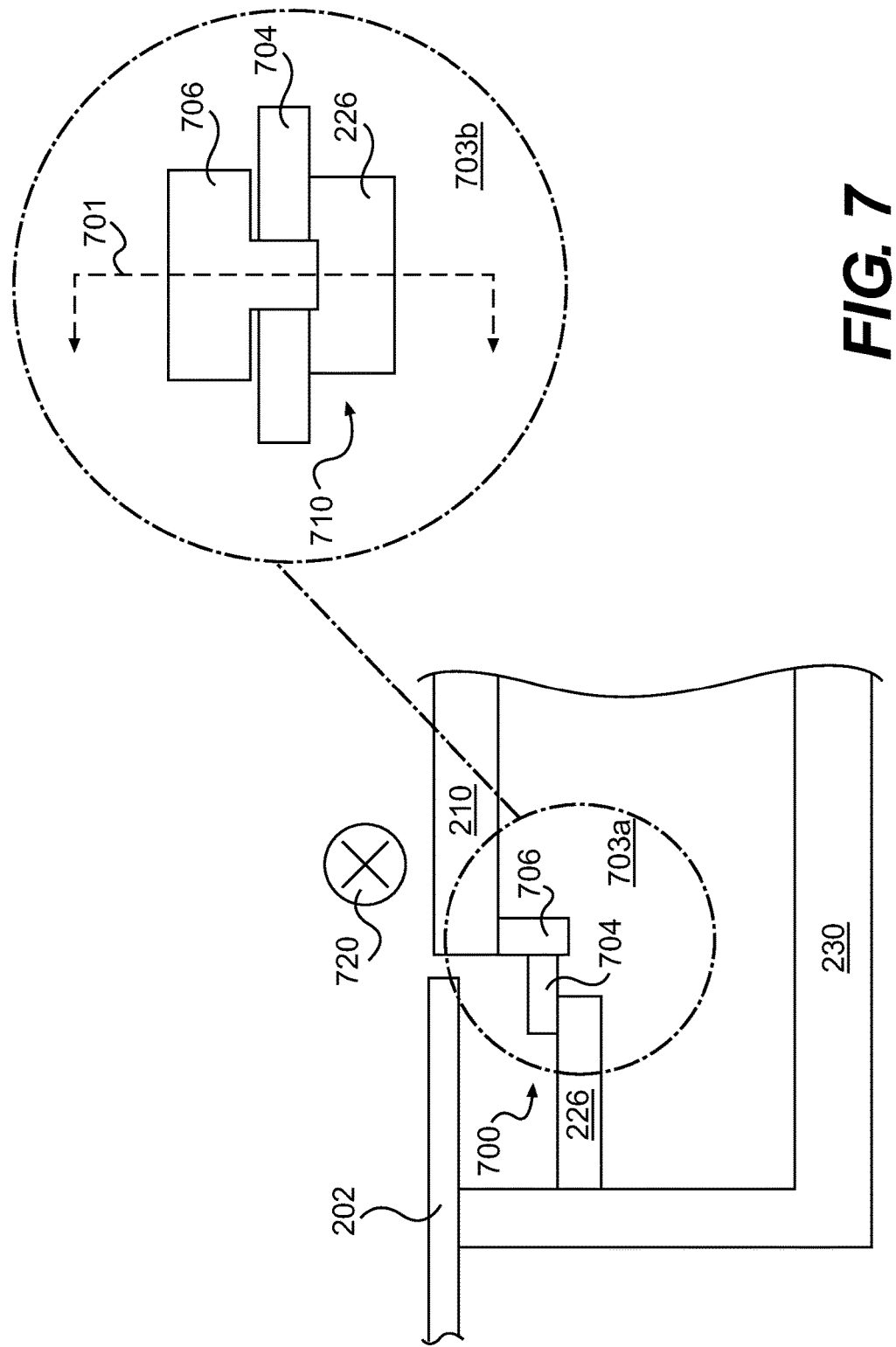
FIG. 7 is a plan view of an example lateral load assembly according to an embodiment of the disclosure.

FIG. 7 is a plan view of an example lateral load assembly 700 that includes a lateral load sensor 226 according to an embodiment of the disclosure. FIG. 7 illustrates lateral load assembly 700 in cross-sectional view 703a and sectioned view 703b sectioned by cutting plane line 701. Frame assembly 230 may be coupled to lateral load sensor 226. Lateral load sensor 226 may be coupled to lateral load sensor mount 704, which may be coupled to t-adaptor 706. As illustrated in sectioned view 703b, a lateral load applied to sensor region 210 (such as when test subject 200 steps onto or off sensor region 210) in a direction illustrated by load direction arrow 720 may cause t-adaptor 706 and lateral load sensor mount 704 to move in load direction 720. From the plan view provided for FIG. 7, load direction arrow 720 is perpendicular to load direction arrow 620 (shown on FIG. 6) and stretches along the plane that extends directly into and out of the view provided. Movement of t-adaptor 706 and lateral load sensor mount 704 in load direction 720 may cause lateral load sensor 226 to measure the lateral load applied in load direction 720.

FIG. 8 is a screenshot illustrating a user interface 800 displaying graphs of load signatures 810, 812, 814, 816, 818, 830, 832, 834, 836, and 838 and/or image capture data 820 according to an embodiment of the disclosure. According to a particular embodiment of the disclosure, graphs of load signatures 810, 812, 814, 816, 818, 830, 832, 834, 836, and 838 may depict the outputs generated by the locomotion analysis plotted as a function of time(s). The depictions may include, but not limited to, graphical representations of the LPs disclosed in Table 1. The graphs of load signatures may illustrate the left and right limbs of test subject 200, such as graphs 810, 812, 814, 816, and 818 represent the left side and graphs 830, 832, 834, 836, and 839 denote the right side of test subject 200. The graphs of load signatures may also include identification of the fore and hind limbs. In addition, image capture data 820, acquired by image capture device 120, may display a video image of the bottom of test subject 200 as it traverses floor plates 210a and 210b. In a particular embodiment of the disclosure, the image capture data 820 may correlate a selected specific load signature from the graphs of load signatures 810, 812, 814, 816, 818, 830, 832, 834, 836, and 838 to display the image capture data 820 associated with the selected specific load signature.

FIG. 9 is a two-dimensional graph illustrating load signatures of limbs from a first side of a test subject according to an embodiment of the disclosure. As described with respect to FIG. 8, an example user interface 800 may include a plurality of assorted graphs of load signatures 810, 812, 814, 816, 818, 830, 832, 834, 836, and 838. In a particular embodiment of the disclosure, the two-dimensional graph may be any of the graphs 810, 812, 814, 816, or 818, which represent the left side of test subject 200. The two-dimensional graph may include, but not limited to, graphical representations of the LPs disclosed in Table 1, which are plotted as a function of time(s). The graphs of load signatures may also identify the fore and hind limbs of the left side of test subject 200.

For example, FIG. 9 presents a plot of measured loads, transformed into magnitude (non-dimensional), in the vertical direction (z-axis) of the left side of a four-legged test subject as a function of frequency (1/seconds). The dashed line represents contact of the left side's fore limb of the test subject; the thick solid line signifies contact of the left side's hind limb; and, the thin solid line denotes contact of both the left side's fore and hind limb. FIG. 9 provides a perspective of the functions of model generation module 308, described with respect to FIG. 3. The plot shows how a test subject traverses the apparatus, making contact at different times with either the fore, hind, or both limbs on the sensor region 210. The model generation module 308 may obtain the data generated by the fore and hind limbs independently and disregard the loads generated by both limbs being in contact. While module generation module 308 may base its analysis on the measurements where both limbs contact the sensor region 210, the data obtained from such analysis requires an undue amount of work to acquire individual fore and hind limb measurements. Thus, to avoid unnecessary analysis, the model generation module 308 utilizes the distinguished data between the fore, hind, and both limbs and analyzes the loads associated only with contact of the fore and hind limbs independently. In addition, FIG. 9 shows the maximum loads imposed by the left side's fore ($Fz_{max}(f)$) and hind ($Fz_{max}(h)$) limbs in the vertical direction. Stance time (S. Time) is also illustrated for the test subject's left rear limb.

FIG. 10 is a two-dimensional graph illustrating load signatures of limbs from a second side of a test subject according to an embodiment of the disclosure. In a particular embodiment of the disclosure, the two-dimensional graph may depict the right side of test subject 200, such as graphs 830, 832, 834, 836, or 838. The two-dimensional graph may illustrate, but note limited to, plots of the LPs disclosed in Table 1 as a function of time(s). In addition, the fore and hind limbs of the right side of test subject 200 may be marked.

For example, similarly to FIG. 9, FIG. 10 illustrates a plot of measured loads, transformed into magnitude (non-dimensional), in the vertical direction (z-axis) of the right side of a four-legged test subject as a function of frequency (1/seconds). The dashed line represents contact of the left side's fore limb of the test subject; the thick solid line signifies contact of the left side's hind limb; and, the thin solid line denotes contact of both the left side's fore and hind limb. As described with respect to FIG. 9, FIG. 10 also demonstrates the model generation module's 308, described with respect to FIG. 3, independent fore and hind limb contact analysis. In addition, FIG. 10 shows the maximum loads imposed by the right side's fore ($Fz_{max}(f)$) and hind ($Fz_{max}(h)$) limbs in the vertical direction. Stance time (S. Time) is also illustrated for the test subject's right rear limb.

The graphical representations of the first and second side by FIG. 9 and FIG. 10, respectively, are interchangeable. In other words, FIG. 9 may depict the right side of test subject 200 and FIG. 10 may represent the left side of test subject 200.

Figure 11:
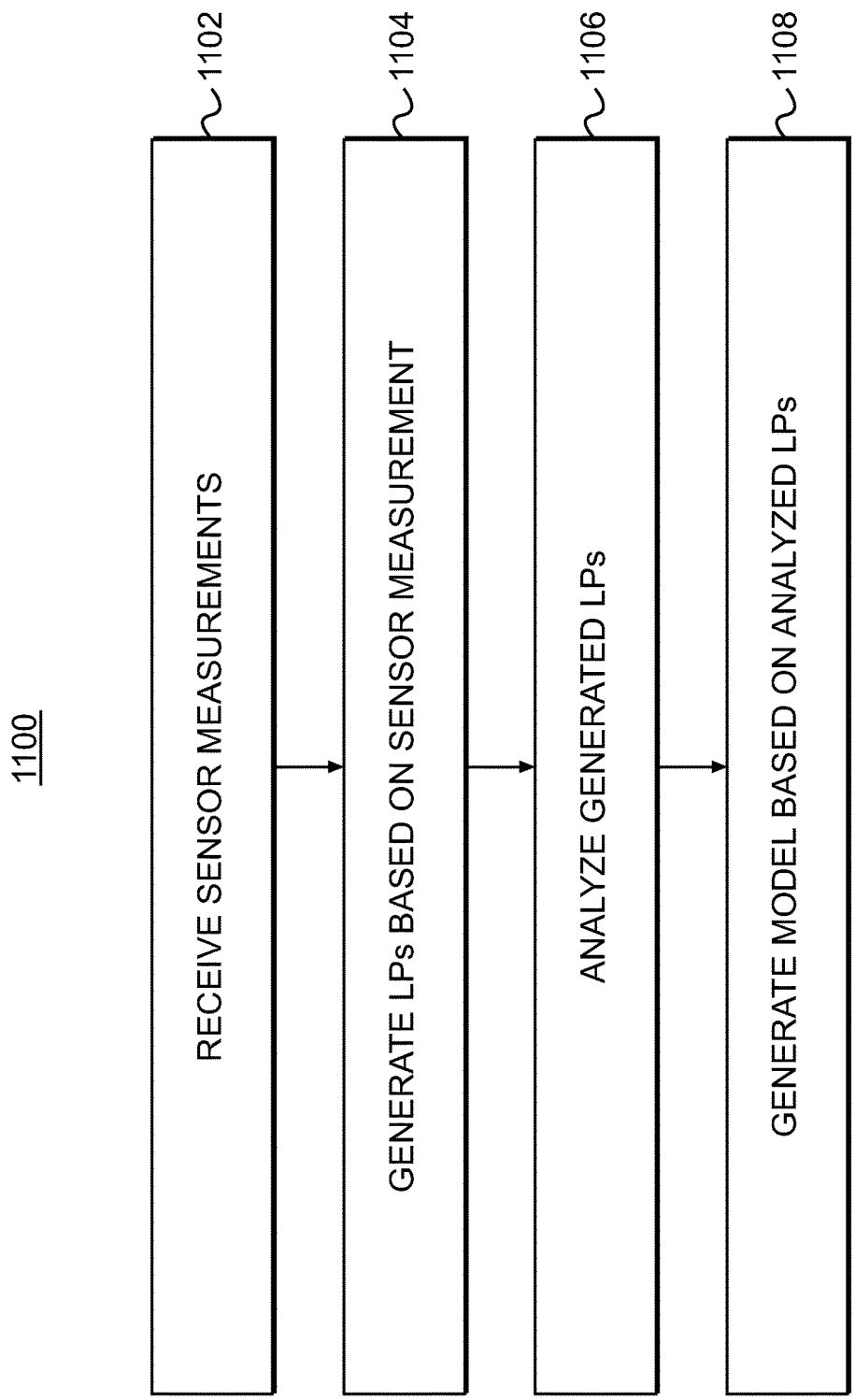
FIG. 11 is a flow diagram of an example process of gait analysis according to an embodiment of the disclosure.

FIG. 11 is a flow diagram of an example process 1100 of gait analysis according to an embodiment of the disclosure. The various processing operations depicted in the flow diagram of FIG. 11 (and in the other drawing figures) are described in greater detail herein. The described operations for a flow diagram may be accomplished using some or all of the system components described in detail above and, in some embodiments, various operations may be performed in different sequences. In other embodiments, additional operations may be performed along with some or all of the operations shown in the depicted flow diagrams. In yet other embodiments, one or more operations may be performed simultaneously. Accordingly, the operations as illustrated (and described in greater detail below) are examples by nature and, as such, should not be viewed as limiting.

According to various embodiments of the disclosure, in an operation 1102, process 1100 may receive a plurality of load measurements from a load measurement apparatus, such as gait analysis apparatus 110. The load measurements may include load measurements selected from among: a vertical load measurement, a for-aft load measurement, and a lateral load measurement. Thus, each type of load measurement may measure a load exerted in a particular direction, thereby enabling robust analysis of the gait of a test subject. In an operation 1104, process 1100 may generate one or more Locomotion Parameters (LPs), examples of which are illustrated in Table 1, based on the received load measurements. Each LP indicates empirical observation of a particular aspect of the gait of the test subject. For example, an LP may indicate a vertical force imposed upon a load sensor, a lateral load imposed upon a load sensor, and a for-aft load imposed upon a load sensor.

In an operation 1106, the LPs may be analyzed. In an operation 1108, a model may be generated based on the analyzed LPs. The model may be a logistic regression model, which is described in example equation (1). The model may indicate probabilities that the analyzed LPs properly predict whether test subject(s) 200 (from which the LPs were derived) suffer(s) from a particular NM disease and/or injury. In this manner, process 1100 may be used to receive and analyze load measurements in order to generate a model that predicts probabilities whether the load measurements indicate that the test subject(s) 200 are properly determined to suffer(s) (or not suffer(s)) from a particular NM disease and/or injury. Alternatively or additionally, the model may be used to determine biomarkers for the particular NM disease and/or injury by identifying particular load measurements and LPs that may be predictive of the particular NM disease and/or injury.

Figure 12:
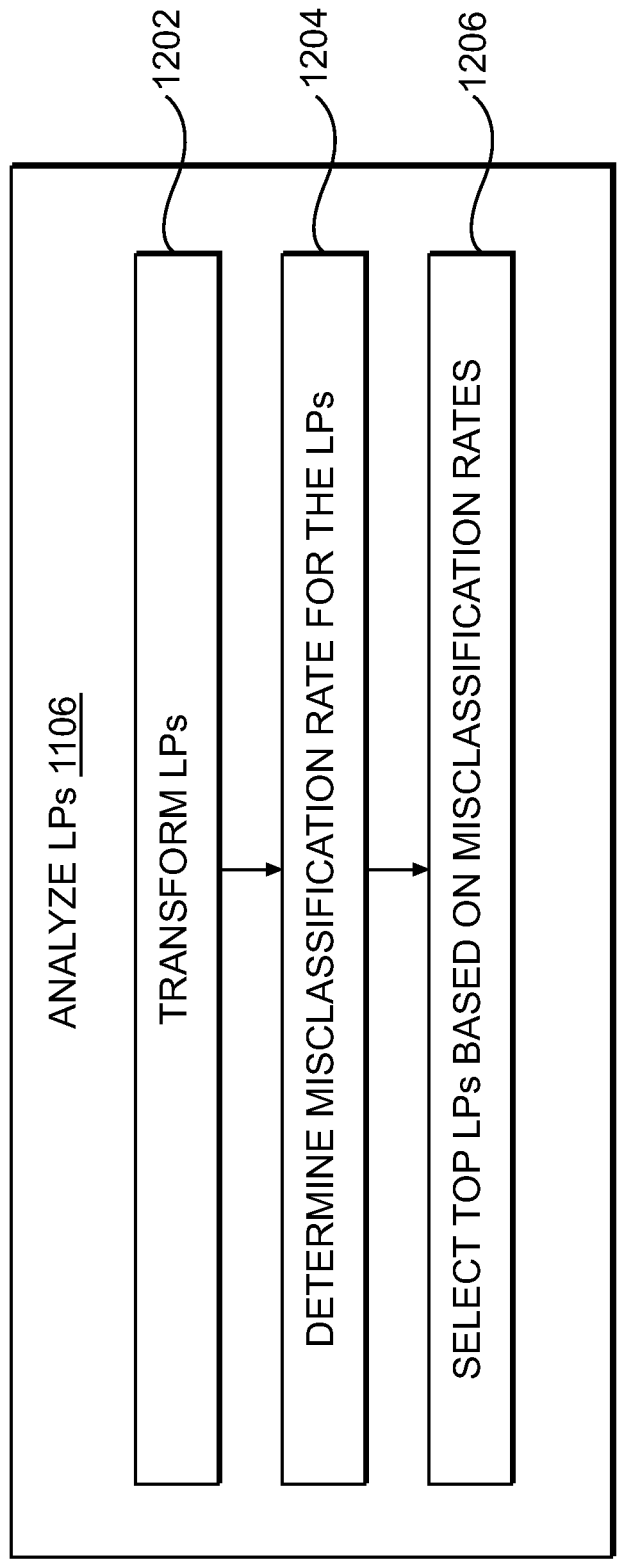
FIG. 12 is a flow diagram of an example process of analyzing locomotion parameters according to an embodiment of the disclosure.

FIG. 12 is a flow diagram of an example process 1106 of analyzing LPs according to an embodiment of the disclosure. According to various embodiments of the disclosure, in an operation 1202, an LP may be a transformed using a statistical transformation, such as entries 5 and 12 of Table 1, which are transformed according to Fourier. Even though statistical transformation of LPs has increased the predictive accuracy of the system, the statistical transformation operation done in 1202 is not an essential element to the analyses of LPs. In an operation 1204, a misclassification rate for each LP may be determined. The misclassification rate may be determined by counting a number of unhealthy test subjects that have been incorrectly predicted to be healthy based on an analysis of each LP as compared to a number of unhealthy test subjects that have been correctly predicted to be unhealthy based on an analysis of each LP. In an operation 1206, based on the misclassification rates, the top LPs may be selected. According to a particular embodiment of the disclosure, the top 6 LPs (having the lowest misclassification rates) may be selected for inclusion into the model. The foregoing is a non-limiting example. For example, any number of the top LPs may be selected and model generation module 308 may iteratively analyze various numbers of top LPs when generating the model. Furthermore, the LPs may be selected on the basis of a predefined threshold (e.g., LPs having misclassification rates below 30%, for example, may be selected for inclusion into the model). The top LPs may be used as biomarkers that identify the particular NM disease and/or injury.

Experimental Results—ALS

The following results were generated using four SOD1-G93A rats that exhibit symptoms of ALS, thereby providing an animal model of ALS, and four Sprague-Dawley (SD) control rats from Taconic Laboratory in Germantown, N.Y. Based on these particular results, seven LPs were identified to be biomarkers of ALS. The biomarkers used in a logistic regression model as described above resulted in faultless distinction between SOD1-G93A group of rats and the SD rats. Table 3 below illustrates 20 measured LPs measured and analyzed during the experiment. Table 4 below illustrates the measured LPs along with associated LP symmetry (LP symmetry may indicate healthy test subjects 200). LP symmetry may be defined using the example equation:

$$LP_{sym} = \frac{LP_{left} - LP_{right}}{LP_{left} + LP_{right}}, \quad (2)$$

$LP_{sym}$ denotes the LP symmetry for a particular LP,
$LP_{left}$ denotes the LP value for a left limb of test subject 200, and
$LP_{right}$ denotes the LP value for a left limb of test subject 200.

This data is run #1 recorded on 21 Mar. 2008 and the rat was 102 days old. Except for Stance Time, $Fz_\omega$, and $Fy_\omega$, all variables are non-dimensional.

TABLE 4

| Locomotion parameter LP | Misclassification rate of LP (%) | Misclassification rate of TLP (%) |
|---|---|---|
| FyB | 34.0 | 18.4 |
| T_$Fy_{max}$ | 33.1 | 20.3 |
| $Fy_{max}$ | 40.5 | 24.5 |
| $Fz_\omega$ | 41.7 | 25.2 |
| $Fz_{mean}$ | 40.5 | 25.8 |
| $Fy_\omega$ | 37.4 | 25.8 |
| NP | 38.6 | 25.8 |
| $Fx_{max}$ | 41.7 | 25.8 |
| $Fz_{max}$ | 42.3 | 26.4 |
| FyP | 41.2 | 26.4 |
| T_$Fy_{min}$ | 39.3 | 27.0 |
| Stance Time | 36.2 | 27.6 |
| $Fy_{min}$ | 38.7 | 27.6 |
| $Fy_{mean}$ | 36.8 | 27.6 |
| Stride | 40.5 | 28.2 |
| $Fx_{mean}$ | 36.6 | 28.2 |
| NB | 38.6 | 28.2 |
| Sym_$Fx_{min}$ | 41.1 | 28.8 |
| T_$Fz_{max}$ | 40.5 | 28.8 |
| Sym_T_$Fy_{max}$ | 41.3 | 29.5 |
| Sym_$Fx_{max}$ | 41.7 | 31.9 |
| Sym_Stance Time | 38.0 | 32.5 |
| $Fx_{min}$ | 42.3 | 32.5 |
| $Fx_\omega$ | 40.5 | 33.1 |
| Sym_T_$Fz_{max}$ | 41.5 | 33.7 |
| Sym_$Fy_{max}$ | 41.1 | 33.7 |
| NPB | 41.8 | 33.7 |
| Sym_$Fz_{mean}$ | 37.4 | 34.4 |
| Sym_$Fz_{max}$ | 42.3 | 35.0 |
| Sym_T_$Fy_{min}$ | 42.0 | 35.0 |
| Sym_$Fy_{mean}$ | 40.5 | 35.0 |
| Sym_$Fz\omega$ | 36.4 | 35.6 |

TABLE 3

| Locomotion parameter (LP) | Left Front Limb | Right Front Limb | Left Hind Limb | Right Hind Limb | Sym_$LP_{Front}$ | Sym_$LP_{Hind}$ |
|---|---|---|---|---|---|---|
| $Fz_{max}$ | 0.7398 | 0.8116 | 0.7357 | 0.7254 | −0.046 | 0.007 |
| Stance Time (s) | 0.1550 | 0.1400 | 0.2900 | 0.1750 | 0.051 | 0.247 |
| T-$Fz_{max}$ | 0.3226 | 0.7500 | 0.2241 | 0.2857 | −0.398 | −0.121 |
| $Fz_{mean}$ | 0.5288 | 0.5260 | 0.4221 | 0.3918 | 0.003 | 0.037 |
| $Fz_\omega$ (s$^{-1}$) | 0.5326 | 0.5280 | 0.5194 | 0.4605 | 0.004 | 0.060 |
| Stride | 0.3463 | 0.7202 | 0.4133 | 0.6818 | −0.351 | −0.245 |
| $Fy_{max}$ | 0.1517 | 0.3986 | 0.0178 | 0.3771 | −0.449 | −0.910 |
| T_$Fy_{max}$ | 0.8710 | 0.1786 | 0.5172 | 0.4571 | 0.660 | 0.062 |
| $Fy_{min}$ | −0.4292 | −0.1286 | −0.1237 | −0.0805 | 0.539 | 0.211 |
| T_$Fy_{min}$ | 0.2258 | 0.5714 | 0.1207 | 0.2857 | −0.434 | −0.406 |
| $Fy_{mean}$ | −0.1504 | 0.0948 | −0.0384 | 0.0660 | 4.411 | −3.779 |
| $Fy_\omega$(s$^{-1}$) | 0.2769 | 0.2621 | 0.0842 | 0.2377 | 0.027 | −0.477 |
| $Fx_{max}$ | 0.0493 | 0.1102 | 0.1040 | 0.1944 | −0.381 | −0.303 |
| $Fx_{min}$ | −0.0462 | −0.0610 | 0.0231 | 0.0163 | −0.138 | 0.175 |
| $Fx_{mean}$ | −0.0005 | 0.0201 | 0.0661 | 0.1093 | −1.048 | −0.246 |
| FyP | 0.0829 | 0.0111 | 0.0118 | 0.0029 | | |
| FyB | −0.1936 | −0.0440 | −0.7466 | −0.1794 | | |
| NP | 5 | 6 | 22 | 23 | | |
| NB | 27 | 53 | 7 | 13 | | |
| NPB | 5 | 2 | 5 | 1 | | |

TABLE 4-continued

| Locomotion parameter LP | Misclassification rate of LP (%) | Misclassification rate of TLP (%) |
|---|---|---|
| Sym_Fx$_{mean}$ | 38.7 | 35.6 |
| Sym_Fy$_{min}$ | 42.0 | 38.7 |
| Sym_Stride | 41.7 | 39.9 |

Table 5 illustrates the top 7 LPs, as presently determined, and each corresponding misclassification rate.

TABLE 5

| TLP (transformed LP) | Misclassification (%) |
|---|---|
| F$_y$B | 18.4 |
| T_Fy$_{max}$ | 20.3 |
| Fy$_{max}$ | 24.5 |
| Fz$_\omega$ | 25.2 |
| Fz$_{mean}$ | 25.8 |
| Fy$_\omega$ | 25.8 |
| NP | 25.8 |

Experimental Results—NM Injury

The following results were generated using ten male Sprague-Dawley (SD) rats. NM injury was introduced to the left hind limb in five of the SD rats by cutting the fibular nerve, which innervates the dorsiflexor muscles. Based on these particular results, six LPs were identified to be biomarkers of NM injury. Table 6 below illustrates 20 measured LPs analyzed for permanently impaired and control rats. Except for stance time, Fz$_\omega$, and Fy$_\omega$, all other variables are non dimensional. Table 7 below illustrates the presently determined top 6 LPs and each corresponding misclassification rate.

TABLE 7

| TLP (transformed LP) | Misclassification (%) |
|---|---|
| Fz$_\omega$ | 26.52 |
| F$_{ymean}$ | 26.89 |
| F$_{xmin}$ | 28.03 |
| NB | 28.03 |
| F$_{zmean}$ | 28.41 |
| NP | 28.79 |

Experimental Results—Parkinson's Disease

For diagnosis and monitoring of Parkinson's disease, Table 8 illustrates the top 7 LPs, presently determined, and each corresponding misclassification rate.

TABLE 8

| TLP (transformed LP) | Misclassification (%) |
|---|---|
| Fy$_{min}$ | 22.48 |
| NP | 24.62 |
| Fx$_{max}$ | 24.62 |
| Fy$_{mean}$ | 25.38 |
| Sym_FyP | 28.41 |
| Fy$_{max}$ | 29.17 |
| NB | 30.3 |

Experimental Results—Temporary Locomotory Impairment

Table 9 below illustrates the recovery of three rats, who were all induced with temporary locomotory impairment on day 0. The probability of locomotory impairment is represented as a numerical value on a 0.0 to 1.0 scale; each given numerical value signifies the likelihood that a specific rat is injured. A 1.0 value denotes an impaired rat and a 0.0 value indicates a healthy (i.e., a recovered) rat. The probability of locomotory impairment was monitored for each rat until all

TABLE 6

| Parameter (LP) | Denervated rat - 12 days after being introduced to permanent locomotory impairment | | | | Control rat | | | |
|---|---|---|---|---|---|---|---|---|
| | Left Front Limb | Right Front Limb | Left Hind Limb | Right Hind Limb | Left Front Limb | Right Front Limb | Left Hind Limb | Right Hind Limb |
| F$_{zmax}$ | 0.6330 | 0.6316 | 0.3628 | 0.8133 | 0.7263 | 0.6801 | 0.4944 | 0.5138 |
| Stance time (s) | 0.1500 | 0.1650 | 0.1750 | 0.3050 | 0.2950 | 0.3000 | 0.8650 | 0.4350 |
| T_F$_{zmax}$ | 0.4000 | 0.3939 | 0.3143 | 0.2295 | 0.3220 | 0.2667 | 0.7052 | 0.1609 |
| F$_{zmean}$ | 0.4015 | 0.4163 | 0.2161 | 0.4614 | 0.3722 | 0.4157 | 0.3541 | 0.4008 |
| F$_{z\omega}$ (1/s) | 0.3946 | 0.4117 | 0.2452 | 0.6158 | 0.6051 | 0.6505 | 0.3941 | 0.3876 |
| Stride | 0.4927 | 0.6649 | 0.4582 | 0.5608 | 0.2381 | 0.4114 | 0.0669 | 0.0676 |
| F$_{ymax}$ | 0.0631 | 0.0405 | 0.0555 | −0.0050 | 0.2079 | 0.3047 | 0.2303 | 0.1440 |
| T_F$_{ymax}$ | 0.9000 | 0.6970 | 0.6857 | 0.0492 | 0.3729 | 0.9500 | 0.7168 | 0.0345 |
| F$_{ymin}$ | −0.1906 | −0.0012 | −0.1433 | −0.3142 | −0.3030 | −0.3995 | −0.0887 | 0.0283 |
| T_F$_{ymin}$ | 0.2333 | 0 | 0.0286 | 0.2787 | 0.4576 | 0.300 | 0.9653 | 1.000 |
| F$_{ymean}$ | 0.0490 | 0.0232 | −0.0351 | −0.0668 | 0.0046 | −0.0180 | 0.0233 | 0.0823 |
| F$_{y\omega}$ | 0.1127 | 0.0247 | 0.0953 | 0.1758 | 0.2529 | 0.2345 | 0.0822 | 0.1084 |
| F$_{xmax}$ | 0.0010 | 0.1322 | 0.0192 | 0.1925 | 0.2225 | 0.1779 | 0.0421 | 0.1726 |
| F$_{xmin}$ | −0.0892 | −0.0150 | −0.0534 | −0.0025 | −0.2698 | −0.1282 | −0.1132 | 0.0444 |
| F$_{xmean}$ | −0.0001 | 0.0626 | 0.0006 | 0.0913 | 0.0156 | 0.0691 | 0.0079 | 0.1180 |
| F$_y$P | 0.0375 | 0.0152 | 0.0338 | 0 | 0.1058 | 0.0956 | 0.0502 | 0.0685 |
| F$_y$B | −0.1115 | −1.0030 | −0.0548 | −0.0248 | −0.0841 | −0.0897 | −0.0367 | 0.0000 |
| NP | 13 | 32 | 8 | 0 | 28 | 31 | 120 | 88 |
| NB | 18 | 2 | 28 | 62 | 32 | 30 | 54 | 0 |
| NPB | 6 | 1 | 2 | 0 | 10 | 3 | 14 | 0 | the rats reached pre-injury levels on the 34th day. The recovery time periods for each injured rat varied, suggesting extrinsic factors, such as pain tolerance, which may affect gait in rats. Thus, Table 9 demonstrates how similar locomotory injury requires differing recovering time courses for an individual rat.

TABLE 9

| Day | Probability of Locomotory Impairment | | |
|-----|--------|--------|--------|
|     | Rat#1  | Rat #2 | Rat #3 |
| 0   | 1.0    | 1.0    | 1.0    |
| 3   | 0.9    | 1.0    | 0.72   |
| 6   | 0.0    | 0.8    | 0.55   |
| 10  | 0.0    | 0.7    | 0.95   |
| 15  | 0.0    | 0.5    | 1.00   |
| 20  | 0.0    | 0.0    | 0.7    |
| 30  | 0.0    | 0.0    | 0.49   |
| 34  | 0.0    | 0.0    | 0.0    |

Examples of GMPD 130 may include any one or more of, for instance, a personal computer, blade server, portable computer, personal digital assistant (PDA), workstation, web-enabled mobile phone, WAP device, web-to-voice device, or other device. Those having skill in the art will appreciate that the embodiments described herein may work with various system configurations. Network 102 may be any network such as, for example, an internet, Ethernet, wireless network, and others.

In addition, various embodiments of the disclosure may be made in hardware, firmware, software, or any suitable combination thereof. Embodiments of the disclosure may also be implemented as instructions stored on a machine-readable medium, which may be read and executed by one or more processors. A machine-readable medium may include any mechanism for storing or transmitting information in a form readable by a machine (e.g., a computing device). For example, a machine-readable storage medium may include read only memory, random access memory, magnetic disk storage media, optical storage media, flash memory devices, and others. Further, firmware, software, routines, or instructions may be described herein in terms of specific example embodiments of the disclosure, and performing certain actions. However, it will be apparent that such descriptions are merely for convenience and that such actions in fact result from computing devices, processors, controllers, or other devices executing the firmware, software, routines, or instructions.

Various embodiments disclosed herein are described as including a particular feature, structure, or characteristic, but every aspect or embodiment may not necessarily include the particular feature, structure, or characteristic. Further, when a particular feature, structure, or characteristic is described in connection with an embodiment, it will be understood that such feature, structure, or characteristic may be included in connection with other embodiments, whether or not explicitly described. Thus, various changes and modifications may be made to the provided description without departing from the scope or spirit of the disclosure.

Other embodiments, uses and features of the present disclosure will be apparent to those skilled in the art from consideration of the specification and practice of the inventive concepts disclosed herein. The specification and drawings should be considered exemplary only, and the scope of the disclosure is accordingly intended to be limited only by the following claims.

What is claimed is:

1. A gait analysis apparatus configured to monitor locomotion comprising:
    a sensor region configured to receive loads generated by a test subject traversing the sensor region;
    a load sensor module comprising one or more load sensors, wherein the load sensor module is configured to measure the loads in a plurality of directions selected from the group consisting of vertical, for-aft, and lateral directions;
    a flexible link configured to suspend the sensor region from the load sensor module in only one of the plurality of directions; and
    one or more limiting members positioned on opposite sides of at least one of the one or more load sensors, wherein the one or more limiting members are coupled to the sensor region and configured to move with the sensor region to limit movement of the sensor region relative to the load sensor module, wherein movement of the one or more limiting members causes the load sensor module to measure the loads in the plurality of directions different from a suspension direction of the sensor region,
    wherein the load sensor module is configured to measure the loads in each of the plurality of directions and to provide each of the respective measurements of the loads to be processed.

2. The gait analysis apparatus of claim 1, wherein the one or more load sensors of the load sensor module comprises:
    at least one for-aft load sensor coupled to the sensor region, wherein the at least one for-aft load sensor is configured to detect a for-aft load on the sensor region and to generate one or more for-aft load measurements in response to the detected for-aft load; and
    at least one lateral load sensor coupled to the sensor region, wherein the at least one lateral load sensor is configured to detect a lateral load on the sensor region and to generate one or more lateral load measurements in response to the detected lateral load,
    wherein each one of the for-aft and lateral load sensors is configured to provide the one or more for-aft load measurements or the one or more lateral load measurements to be processed.

3. The gait analysis apparatus of claim 2, wherein the one or more load sensors of the load sensor module comprises:
    at least one vertical load sensor coupled to the sensor region, wherein the at least one vertical load sensor is configured to detect a vertical load on the sensor region and to generate one or more vertical load measurements in response to the detected vertical load,
    wherein each one of the vertical load sensors is configured to provide the one or more vertical load measurements to be processed.

4. The gait analysis apparatus of claim 1, wherein the one or more load sensors of the load sensor module comprises:
    a plurality of single-axis load sensors selected from the group consisting of at least one for-aft load sensor configured to measure the loads in the for-aft direction, at least one lateral load sensor configured to measure the loads in the lateral direction, and at least one vertical load sensor configured to measure the loads in the vertical direction,
    wherein each one of the single-axis load sensors is configured to provide each of the respective measurements of the loads to be processed.

5. The gait analysis apparatus of claim 1, wherein the sensor region comprises a first floor plate and a second floor plate that are disposed adjacently to one another, wherein the first floor plate is configured to be moved independently of the second floor plate.

6. The gait analysis apparatus of claim 5, wherein the first floor plate and the second floor plate are each coupled to a respective load sensor module.

7. The gait analysis apparatus of claim 5, wherein the first floor plate and the second floor plate are substantially rectangular.

8. The gait analysis apparatus of claim 5, wherein the first floor plate comprises four vertical load sensors as all or a portion of the one or more load sensors, each disposed at different portions of the first floor plate.

9. The gait analysis apparatus of claim 5, wherein the first floor plate comprises two lateral load sensors as all or a portion of the one or more load sensors, each disposed at either ends of the first floor plate.

10. The gait analysis apparatus of claim 5, wherein the first floor plate comprises one for-aft load sensor as all or a portion of the one or more load sensors, wherein the one for-aft load sensor is disposed along an edge portion of the first floor plate.

11. The gait analysis apparatus of claim 5, wherein the second floor plate comprises four vertical load sensors as all or a portion of the one or more load sensors, wherein the four vertical load sensors are each disposed at different portions of the second floor plate.

12. The gait analysis apparatus of claim 5, wherein the second floor plate comprises two lateral load sensors as a portion of the one or more load sensors, each disposed at opposite ends of the second floor plate.

13. The gait analysis apparatus of claim 5, wherein the second floor plate comprises one for-aft load sensor as a portion of the one or more load sensors, wherein the one for-aft load sensor is disposed along an edge portion of the second floor plate.

14. The gait analysis apparatus of claim 1 further comprising a limb placement detection system configured to distinguish the measured loads associated with a specific limb of the test subject, the limb placement detection system includes:
a plurality of lights configured to highlight a contact location of the specific limb of the test subject; and
an image capture device configured to generate one or more images of the test subject as the test subject traverses the sensor region,
wherein the plurality of lights is dispersed along the surface of the sensor region, and
wherein the sensor region is a transparent material to the image capture device such that the image capture device is able to generate the one or more images through the sensor region.

15. The gait analysis apparatus of claim 14, wherein the plurality of lights and the image capture device have infrared capabilities.

16. The gait analysis apparatus of claim 14, wherein the image capture device is a video camera device.

17. The gait analysis apparatus of claim 14, wherein the transparent material is plexi-glass.

18. The gait analysis apparatus of claim 1, wherein the gait analysis apparatus includes a gait measurement processing device which receives the respective measurements of the loads to be processed, the gait measurement processing device comprising one or more processors programmed to implement instructions to:
receive at least two types of first load measurements associated with a first type of locomotion of a first test subject;
generate a first plurality of locomotion parameters (LPs) based on the at least two types of first load measurements;
generate a probability model based on the first plurality of LPs;
upon generating the probability model, receive at least two types of second load measurements associated with a second type of locomotion of a second test subject;
generate a second plurality of LPs based on the at least two types of second load measurements corresponding to the first plurality of LPs;
compare each one of the first plurality of LPs with each one of the corresponding second plurality of LPs based on the probability model; and
determine a plurality of biomarkers that predict one of the types of locomotion based on the comparison.

19. The gait analysis apparatus of claim 18, wherein the at least two types of first load measurements are selected from the group consisting of a vertical load measurement that measures a vertical load imposed by the first test subject, a lateral load measurement that measures a lateral load imposed by the first test subject, and a for-aft load measurement that measures a for-aft load imposed by the first test subject.

20. The gait analysis apparatus of claim 18, wherein the one or more processors are further programmed to implement instructions to:
transform each one of the first plurality of LPs and each one of the corresponding second plurality of LPs.

21. The gait analysis apparatus of claim 20, wherein said transform is a spline transformation.

22. The gait analysis apparatus of claim 20, wherein said transform is a Fourier transformation.

23. The gait analysis apparatus of claim 18, wherein the first type of locomotion is healthy locomotion and the second type of locomotion is impaired locomotion.

24. The gait analysis apparatus of claim 18, wherein the first type of locomotion is impaired locomotion and the second type of locomotion is healthy locomotion.

25. The gait analysis apparatus of claim 18, wherein the one or more processors are further programmed to implement instructions to:
upon determining the plurality of biomarkers, receive at least two types of third load measurements associated with a third type of locomotion of a third test subject;
generate a third plurality of LPs based on the at least two types of third load measurements corresponding to the plurality of biomarkers; and
compare each of the plurality of biomarkers with each of the corresponding third plurality of LPs in order to diagnosis the third test subject,
wherein the third type of locomotion of the third test subject is unknown.

26. The gait analysis apparatus of claim 18, wherein the one or more processors are further programmed to implement instructions to:
receive one or more images of the first test subject associated with the at least two types of first load measurements; and
generate the first plurality of LPs based on the received one or more images.

27. The gait analysis apparatus of claim 26, wherein the one or more processors are further programmed to implement instructions to:

display the one or more images;
correlate at least one of the at least two types of first load measurements to one or more limbs of the first test subject;
correlate at least one of the at least two types of second load measurements to one or more limbs of the second test subject.

28. The gait analysis apparatus of claim 1, wherein the one or more load sensors of the load sensor module comprises a plurality of load cells, which includes:
at least one for-aft load sensor coupled to the sensor region, wherein the at least one for-aft load sensor is configured to detect a for-aft load on the sensor region and to generate one or more for-aft load measurements in response to the detected for-aft load; and
at least one vertical load sensor coupled to the sensor region, wherein the at least one vertical load sensor is configured to detect a vertical load on the sensor region and to generate one or more vertical load measurements in response to the detected vertical load;
wherein each one of the for-aft and vertical load sensors is configured to provide one or more for-aft load measurements or the one or more vertical load measurements to be processed.

29. The gait analysis apparatus of claim 1, wherein the one or more load sensors of the load sensor module comprises a plurality of load cells, which includes:
at least one vertical load sensor coupled to the sensor region, wherein the at least one vertical load sensor is configured to detect a vertical load on the sensor region and to generate one or more vertical load measurements in response to the detected vertical load; and
at least one lateral load sensor coupled to the sensor region, wherein the at least one lateral load sensor is configured to detect a lateral load on the sensor region and to generate one or more lateral load measurements in response to the detected lateral load;
wherein each one of the vertical and lateral load sensors is configured to provide the one or more vertical load measurements or the one or more lateral load measurements to be processed.

30. The gait analysis apparatus of claim 1, wherein the flexible link is one of a string, a wire, a rope, a cable, and a chain.

31. The gait analysis apparatus of claim 1, wherein the one or more limiting members include set screws coupled to a bracket, wherein the bracket extends between the opposite sides of the at least one of the one or more load sensors.

32. The gait analysis apparatus of claim 1, wherein the one or more limiting members include a load sensor mount coupled to a t-adaptor.

33. A system for gait analysis comprising:
a gait measurement processing device;
a gait analysis apparatus operatively coupled to the gait measurement processing device, comprising:
a first floor plate and a second floor plate that are disposed adjacently to one another, wherein the first floor plate is configured to be moved independently of the second floor plate;
at least one vertical load sensor coupled to each of the first floor plate and the second floor plate, wherein the at least one vertical load sensor is configured to detect a vertical load on either or both of the first floor plate and the second floor plate and to generate one or more vertical load measurements in response to the detected vertical load;
a flexible link configured to suspend each of the first floor plate and the second floor plate in a vertical direction;
at least one for-aft load sensor coupled to each of the first floor plate and the second floor plate, wherein the at least one for-aft load sensor is configured to detect a for-aft load on either or both of the first floor plate and the second floor plate;
at least one first limiting member coupled to each of said first floor plate and said second floor plate configured to move with and limit for-aft movement of each of the first floor plate and the second floor plate, wherein for-aft movement of one or more of the first and second floor plate causes said at least one for-aft load sensor to one or more for-aft load measurements in response to the detected for-aft load;
at least one lateral load sensor coupled to each of the first floor plate and the second floor plate, wherein the at least one lateral load sensor is configured to detect a lateral load on either or both of the first floor plate and the second floor plate; and
at least one second limiting member coupled to each of said first floor plate and said second floor plate configured to move with and limit movement of each of the first floor plate and the second floor plate, wherein lateral movement of one or more of the first and second floor plate causes said at least one lateral load sensor to generate one or more lateral load measurements in response to the detected lateral load,
wherein at least one of the at least one first limiting member or the at least one second limiting member is positioned respectively on opposite sides of the at least one for-aft load sensor or the at least one lateral load sensor,
wherein the at least one vertical load sensor is configured to provide the one or more vertical load measurements to the gait measurement processing device, the at least one for-aft load sensor is configured to provide the one or more for-aft load measurements to the gait measurement processing device, and the at least one lateral load sensor is configured to provide the one or more lateral load measurements to the gait measuring processing device, and
wherein the gait measurement processing device comprises one or more processors programmed to implement instructions to:
receive the vertical load measurements, the for-aft load measurements and the lateral load measurements;
generate a plurality of locomotion parameters (LPs) based on the received load measurements;
analyze the plurality of LPs; and
generate a probability model based on the analysis.

* * * * *